US010994268B2

(12) United States Patent
Iaccino et al.

(10) Patent No.: US 10,994,268 B2
(45) Date of Patent: May 4, 2021

(54) PROCESSES FOR REJUVENATING CATALYSTS

(71) Applicant: ExxonMobil Chemical Patents Inc., Baytown, TX (US)

(72) Inventors: Larry L. Iaccino, Seabrook, TX (US); Xiaoying Bao, Houston, TX (US); Jeremy W. Bedard, Humble, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 609 days.

(21) Appl. No.: 15/947,986

(22) Filed: Apr. 9, 2018

(65) Prior Publication Data

US 2018/0318813 A1 Nov. 8, 2018

Related U.S. Application Data

(60) Provisional application No. 62/500,805, filed on May 3, 2017.

(51) Int. Cl.

| | | |
|---|---|---|
| *B01J 29/90* | (2006.01) | |
| *B01J 29/44* | (2006.01) | |
| *B01J 29/40* | (2006.01) | |
| *C07C 5/41* | (2006.01) | |
| *C07C 5/32* | (2006.01) | |
| *C07C 5/333* | (2006.01) | |
| *B01J 38/02* | (2006.01) | |
| *C07C 5/373* | (2006.01) | |
| *B01J 38/18* | (2006.01) | |
| *B01J 38/14* | (2006.01) | |

(52) U.S. Cl.
CPC .............. *B01J 29/90* (2013.01); *B01J 29/405* (2013.01); *B01J 29/44* (2013.01); *B01J 38/02* (2013.01); *B01J 38/18* (2013.01); *C07C 5/325* (2013.01); *C07C 5/333* (2013.01); *C07C 5/3337* (2013.01); *C07C 5/373* (2013.01); *C07C 5/417* (2013.01); *B01J 38/14* (2013.01); *C07C 2529/44* (2013.01); *C07C 2529/46* (2013.01)

(58) Field of Classification Search
CPC . B01J 29/90; B01J 29/405; B01J 29/44; B01J 38/02; B01J 38/14; C07C 5/325; C07C 5/3337; C07C 5/417
USPC .......................................................... 502/38
See application file for complete search history.

(56) References Cited

U.S. PATENT DOCUMENTS

| | | |
|---|---|---|
| 3,836,597 A | 9/1974 | Sie |
| 4,300,014 A | 11/1981 | Yamasaki et al. |
| 4,600,700 A | 7/1986 | McHale |
| 4,795,845 A | 1/1989 | Martindale et al. |
| 5,393,717 A | 2/1995 | Apelian et al. |
| 5,883,031 A | 3/1999 | Innes et al. |
| 2005/0187095 A1 | 8/2005 | Grey et al. |
| 2010/0248943 A1 | 9/2010 | Bozanno |
| 2013/0231511 A1 | 9/2013 | Wu |

*Primary Examiner* — Edward M Johnson

(57) ABSTRACT

Disclosed are processes for rejuvenating catalysts comprising at least one Group 10 metal and a microporous crystalline metallosilicate, and hydrocarbon conversion processes including such rejuvenation processes. In an aspect, the rejuvenation process comprises contacting a deactivated catalyst comprising at least one Group 10 metal and a microporous crystalline metallosilicate with an oxygen-containing gaseous stream under conditions comprising a temperature ranging from about 250° C. to about 375° C. and a pressure of up to about 100 bar. In a further aspect, the rejuvenation process comprises contacting a deactivated catalyst comprising at least one Group 10 metal, at least one rare earth metal, and a microporous crystalline metallosilicate with an oxygen-containing gaseous stream under conditions comprising a temperature ranging from about 250° C. to about 500° C. and a pressure of up to about 100 bar.

25 Claims, 10 Drawing Sheets

PROCESSES FOR REJUVENATING CATALYSTS

CROSS-REFERENCE TO RELATED APPLICATION

This application claims priority to U.S. Provisional Application Ser. No. 62/500,805, filed May 3, 2017, the disclosures of which is incorporated herein by reference.

FIELD OF THE INVENTION

The present invention relates to processes for rejuvenating catalysts comprising a Group 10 metal and a microporous crystalline metallosilicate.

BACKGROUND OF THE INVENTION

Supported noble metal, e.g., platinum containing catalysts are widely utilized in hydrocarbon conversion processes. Such catalysts generally lose activity over time, in large part due to the formation of coke. When the activity of the catalyst is reduced to an unsatisfactory level, the catalyst must be discarded or more preferably, reconditioned or regenerated so that it can be reused.

Conventional catalyst regeneration methods for supported noble metal catalysts typically comprise burning coke off the catalyst under oxidation conditions sufficient to remove substantially all of the coke from the catalyst. However, the severe conditions, e.g., elevated temperature, of these conventional oxidative coke removal methods generally result in agglomeration of the supported metal particles. Oxychlorination may be used to re-disperse the agglomerated noble metal particles, but is time consuming and leads to progressive deterioration in the substrate.

Coke removal methods performed under less severe conditions have been described for noble metal containing catalysts on a molecular sieve. Some references of potential interest in this regard may include: U.S. Pat. Nos. 5,883,031 and 5,393,717. There remains a continuing need, however, for methods of removing coke from supported noble metal catalysts that are performed under mild conditions.

SUMMARY OF THE INVENTION

The present invention relates to processes for rejuvenating catalysts comprising a Group 10 metal and a microporous crystalline metallosilicate that address the need for methods of removing coke from such catalysts under mild conditions.

In a first aspect, the invention relates to a process for rejuvenating a deactivated catalyst comprising at least one Group 10 metal and a microporous crystalline metallosilicate. The process comprises contacting the catalyst with an oxygen-containing gaseous stream under conditions comprising a temperature ranging from about 250° C. to about 375° C. and a pressure of up to about 100 bar.

In another aspect, the invention relates to a process for rejuvenating a deactivated catalyst comprising at least one Group 10 metal, at least one rare earth metal, and a microporous crystalline metallosilicate. The process comprises contacting the catalyst with an oxygen-containing gaseous stream under conditions comprising a temperature ranging from about 250° C. to about 500° C. and a pressure of up to about 100 bar.

The invention further relates to processes for the chemical conversion of a hydrocarbon feedstock.

In a first aspect, the hydrocarbon conversion process comprises contacting a hydrocarbon feedstock with a catalyst comprising at least one Group 10 metal and a microporous crystalline metallosilicate in a reaction zone to form a hydrocarbon reaction product. In such aspects, the process further comprise the steps forming deactivated catalyst from the catalyst and rejuvenating the deactivated catalyst comprising contacting the catalyst with an oxygen-containing gaseous stream under conditions comprising a temperature ranging from about 250° C. to about 375° C. and a pressure of up to about 100 bar.

In a further aspect, the process comprises the step of contacting a hydrocarbon feedstock with a catalyst comprising at least one Group 10 metal, at least one rare earth metal, and a microporous crystalline metallosilicate in a reaction zone to form a hydrocarbon reaction product. In such aspects, the process further comprises the steps of forming deactivated catalyst from the catalyst and rejuvenating the deactivated catalyst comprising contacting the catalyst with an oxygen-containing gaseous stream under conditions comprising a temperature ranging from about 250° C. to about 500° C. and a pressure of up to about 100 bar.

DETAILED DESCRIPTION OF THE PREFERRED EMBODIMENTS

Figure 1A:
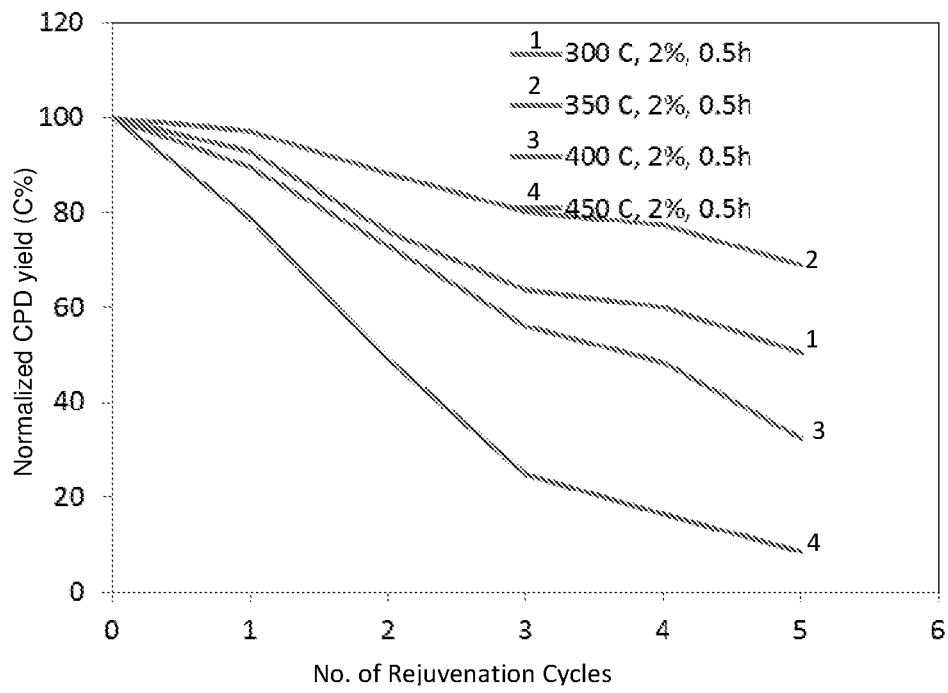
FIG. 1A and FIG. 1B show the normalized cyclopentadiene (CPD) yield and cyclic $C_5$ hydrocarbon selectivity against the number of rejuvenation cycles resulting from the performance evaluation conducted in Example 8 of catalyst rejuvenated using an oxygen-containing gaseous stream having an oxygen concentration of 2 vol % at a variety of temperatures.

Disclosed herein are processes useful in rejuvenating noble metal-containing metallosilicate catalysts which have lost activity during a hydrocarbon conversion processing step due to coke buildup. The present methods are particularly suitable in hydrocarbon conversion processes comprising the conversion of acyclic hydrocarbons to alkenes, cyclics, and/or aromatics.

All numerical values within the detailed description and the claims herein are modified by "about" or "approximately" the indicated value, and take into account experimental error and variations that would be expected by a person having ordinary skill in the art. Unless otherwise indicated, room temperature is about 23° C.

Definitions

For the purpose of this specification and appended claims, the following terms are defined.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n. The term "$C_n$" means hydrocarbon(s) having n carbon atom(s) per molecule, wherein n is a positive integer.

As used herein, the term "light hydrocarbon" means light paraffinic and/or olefinic hydrocarbons comprised substantially of hydrogen and carbon only and has one to no more than 4 carbon atoms.

The term "saturates" includes, but is not limited to, alkanes and cycloalkanes.

The term "non-saturates" includes, but is not limited to, alkenes, dialkenes, alkynes, cyclo-alkenes and cyclo-dialkenes.

The term "cyclic hydrocarbon" denotes groups such as the cyclopropane, cyclopropene, cyclobutane, cyclobutadiene, etc., and substituted analogues of these structures. These cyclic hydrocarbons can be single- or multi-ring structures. Preferably, the term "cyclic hydrocarbon" refers to non-aromatics.

The term "cyclic $C_5$" or "$cC_5$" includes, but is not limited to, cyclopentane, cyclopentene, cyclopentadiene, and mixtures of two or more thereof. The term "cyclic $C_5$" or "$cC_5$" also includes alkylated analogs of any of the foregoing, e.g., methyl cyclopentane, methyl cyclopentene, and methyl cyclopentadiene. It should be recognized for purposes of the invention that cyclopentadiene (CPD) spontaneously dimerizes over time to form dicyclopentadiene (DCPD) via Diels-Alder condensation over a range of conditions, including ambient temperature and pressure.

The term "acyclics" includes, but is not limited to, linear and branched saturates and non-saturates.

The term "alkane" refers to non-aromatic saturated hydrocarbons with the general formula $C_nH_{(2n+2)}$, where n is 1 or greater. An alkane may be straight chained or branched. Examples of alkanes include, but are not limited to methane, ethane, propane, butane, pentane, hexane, heptane and octane. "Alkane" is intended to embrace all structural isomeric forms of an alkane. For example, butane encompasses n-butane and isobutane; pentane encompasses n-pentane, isopentane and neopentane.

The term "alkene," alternatively referred to as "olefin," refers to a branched or unbranched unsaturated hydrocarbon having one or more carbon-carbon double bonds. A simple alkene comprises the general formula $C_nH_{2n}$, where n is 2 or greater. Examples of alkenes include, but are not limited to ethylene, propylene, butylene, pentene, hexene and heptene. "Alkene" is intended to embrace all structural isomeric forms of an alkene. For example, butylene encompasses but-1-ene, (Z)-but-2-ene, etc.

The term "aromatic" means a planar cyclic hydrocarbyl with conjugated double bonds, such as, for example, benzene. As used herein, the term aromatic encompasses compounds containing one or more aromatic rings, including, but not limited to, benzene, toluene, and xylene, and polynuclear aromatics (PNAs), which include, but are not limited to, naphthalene, anthracene, chrysene, and their alkylated versions. The term "$C_{6+}$ aromatics" includes compounds based upon an aromatic ring having six or more ring atoms, including, but not limited to, benzene, toluene, and xylene and polynuclear aromatics (PNAs) which include, but are not limited to, naphthalene, anthracene, chrysene, and their alkylated versions.

The term "BTX" includes, but is not limited to, a mixture of benzene, toluene, and xylene (ortho and/or meta and/or para).

The term "coke" includes, but is not limited to, a low hydrogen content hydrocarbon that is adsorbed on the catalyst composition.

The term "$C_{n+}$" means hydrocarbon(s) having at least n carbon atom(s) per molecule.

The term "$C_{n-}$" means hydrocarbon(s) having no more than n carbon atom(s) per molecule.

The term "$C_5$ feedstock" includes a feedstock containing n-pentane, such as, for example, a feedstock which is predominately normal pentane and isopentane (also referred to as methylbutane), with smaller fractions of cyclopentane and neopentane (also referred to as 2,2-dimethylpropane).

All numbers and references to the Periodic Table of Elements are based on the new notation as set out in Chemical and Engineering News, 63(5), 27, (1985), unless otherwise specified.

The term "Group 10 metal" means an element in Group 10 of the Periodic Table and includes, but is not limited to, nickel, palladium, platinum, and a mixture of two or more thereof.

The term "Group 11 metal" means an element in Group 11 of the Periodic Table and includes, but is not limited to, copper, silver, gold, and a mixture of two or more thereof.

The term "Group 1 alkali metal" means an element in Group 1 of the Periodic Table and includes, but is not limited to, lithium, sodium, potassium, rubidium, cesium, and a mixture of two or more thereof, and excludes hydrogen.

The term "Group 2 alkaline earth metal" means an element in Group 2 of the Periodic Table and includes, but is not limited to, beryllium, magnesium, calcium, strontium, barium, and a mixture of two or more thereof.

The term "rare earth metal" means an element in the Lanthanide series of the Periodic Table, as well as scandium and yttrium. The term rare earth metal includes, but is not limited to, lanthanum, praseodymium, neodymium, cerium, yttrium, and a mixture of two or more thereof.

The term "constraint index" is defined in U.S. Pat. Nos. 3,972,832 and 4,016,218, both of which are incorporated herein by reference.

As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types," Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks may be in a regular fashion, an irregular fashion, a random fashion, or any combination thereof; and molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

As used herein, the term "molecular sieve" is used synonymously with the term "zeolite" or "microporous crystalline material."

As used herein, the term "selectivity" means the moles of carbon in the respective cyclic $C_5$, CPD, $C_1$, and $C_{2-4}$ formed divided by total moles of carbon in the pentane converted. For example, the term "carbon selectivity to cyclic $C_5$ of at least 30%" means that at least 30 moles of carbon in the cyclic $C_5$ is formed per 100 moles of carbon in the pentane converted.

As used herein, the term "conversion" means the moles of carbon in the acyclic $C_5$ feedstock that is converted to a product. The term "conversion of at least 70% of said acyclic $C_5$ feedstock to a product" means that at least 70% of the moles of said acyclic $C_5$ feedstock was converted to a product.

As used herein, the term "Alpha Value" is used as a measure of the cracking activity of a catalyst and is described in U.S. Pat. No. 3,354,078; in the Journal of Catalysis, Vol. 4, p. 527 (1965); Vol. 6, p. 278, (1966); and Vol. 61, p. 395, (1980), each incorporated herein by reference. The experimental conditions of the test used herein included a constant temperature of 538° C. and a variable flow rate as described in detail in the Journal of Catalysis, Vol. 61, p. 395, (1980).

As used herein, "deactivated catalyst" refers to catalyst that has lost activity during the course of a hydrocarbon conversion process, e.g., due to the accumulation of coke and/or agglomeration of metal.

As used herein, "regenerated catalyst" and "rejuvenated catalyst" refer to deactivated catalyst that has been treated to restore at least a portion of the lost activity. Regenerated catalyst refers to catalyst that has been treated in the presence of chlorine.

As used herein, the term "reactor system" refers to a system including one or more reactors and all optional equipment used in the production of cyclopentadiene.

As used herein, the term "reactor" refers to any vessel(s) in which a chemical reaction occurs. Reactor includes both distinct reactors, as well as reaction zones within a single reactor apparatus and, as applicable, reactions zones across multiple reactors. For example, a single reactor may have multiple reaction zones. Where the description refers to a first and second reactor, the person of ordinary skill in the art will readily recognize such reference includes two reactors, as well as a single reactor vessel having first and second reaction zones. Likewise, a first reactor effluent and a second reactor effluent will be recognized to include the effluent from the first reaction zone and the second reaction zone of a single reactor, respectively.

A reactor/reaction zone may be an adiabatic reactor/reaction zone or a diabatic reactor/reaction zone. As used herein, the term "adiabatic" refers to a reaction zone for which there is essentially no heat input into the system other than by a flowing process fluid. A reaction zone that has unavoidable losses due to conduction and/or radiation may also be considered adiabatic for the purpose of this invention. As used herein, the term "diabatic" refers to a reactor/reaction zone to which heat is supplied by a means in addition to that provided by the flowing process fluid.

As used herein, the term "moving bed" reactor refers to a zone or vessel with contacting of solids (e.g., catalyst particles) and gas flows such that the superficial gas velocity (U) is below the velocity required for dilute-phase pneumatic conveying of solid particles in order to maintain a solids bed with void fraction below 95%. In a moving bed reactor, the solids (e.g., catalyst material) may slowly travel through the reactor and may be removed from the bottom of the reactor and added to the top of the reactor. A moving bed reactor may operate under several flow regimes, including settling or moving packed-bed regime ($U<U_{mf}$), bubbling regime ($U_{mf}<U<U_{mb}$), slugging regime ($U_{mb}<U<U_c$), transition to and turbulent fluidization regime ($U_c<U<U_{tr}$), and fast-fluidization regime ($U>U_{tr}$), where $U_{mf}$ is minimum fluidizing velocity, $U_{mb}$ is minimum bubbling velocity, $U_c$ is the velocity at which fluctuation in pressure peaks, and tr is transport velocity. These different fluidization regimes have been described in, for example, Kunii, D., Levenspiel, O., Chapter 3 of *Fluidization Engineering, 2$^{nd}$ Edition*, Butterworth-Heinemann, Boston, 1991 and Walas, S. M., Chapter 6 of *Chemical Process Equipment*, Revised 2nd Edition, Butterworth-Heinemann, Boston, 2010, which are incorporated by reference.

As used herein, the term "settling bed" reactor refers to a zone or vessel wherein particulates contact with gas flows such that the superficial gas velocity (U) is below the minimum velocity required to fluidize the solid particles (e.g., catalyst particles), the minimum fluidization velocity ($U_{mf}$), $U<U_{mf}$, in at least a portion of the reaction zone, and/or operating at a velocity higher than the minimum fluidization velocity, while maintaining a gradient in gas and/or solid property (such as, temperature, gas, or solid composition, etc.) axially up the reactor bed by using reactor internals to minimize gas-solid back-mixing. Description of the minimum fluidization velocity is given in, for example, Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Revised 2nd Edition, Butterworth-Heinemann, Boston, 2010. A settling bed reactor may be a "circulating settling bed reactor," which refers to a settling bed with a movement of solids (e.g., catalyst material) through the reactor and at least a partial recirculation of the solids (e.g., catalyst material). For example, the solids (e.g., catalyst material) may have been removed from the reactor, regenerated, reheated, and/or separated from the product stream and then returned back to the reactor.

As used herein, the term "fluidized bed" reactor refers to a zone or vessel with contacting of solids (e.g., catalyst particles) and gas flows such that the superficial gas velocity (U) is sufficient to fluidize solid particles (i.e., above the minimum fluidization velocity $U_{mf}$) and is below the velocity required for dilute-phase pneumatic conveying of solid particles in order to maintain a solids bed with void fraction below 95%. As used herein, the term "cascaded fluid-beds" means a series arrangement of individual fluid-beds such that there can be a gradient in gas and/or solid property (such as, temperature, gas, or solid composition, pressure, etc.) as the solid or gas cascades from one fluid-bed to another. Locus of minimum fluidization velocity is given in, for example, Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Revised $2^{nd}$ Edition, Butterworth-Heinemann, Boston, 2010. A fluidized bed reactor may be a moving fluidized bed reactor, such as a "circulating fluidized bed reactor," which refers to a fluidized bed with a movement of solids (e.g., catalyst material) through the reactor and at least a partial recirculation of the solids (e.g., catalyst material). For example, the solids (e.g., catalyst material) may have been removed from the reactor, regenerated, reheated, and/or separated from the product stream and then returned back to the reactor. Additionally, a fluidized bed reactor may be a "captive fluidized bed reactor" wherein solids (e.g., catalyst material) may circulate between reaction zones but are not circulated, on a continuous flow basis, between the reactor and a separate vessel (e.g., to perform re-heating and/or regeneration). Solids (e.g., catalyst material) may be withdrawn from the reactor and returned (along with any fresh solids addition) to the reactor after batchwise regeneration performed in a separate vessel. Also, presence of an external cyclone (or any similar device to separate solids from the reactor effluent stream) and its return standpipe is considered part of the captive fluidized bed reactor, i.e., does not constitute a separate vessel for the purpose of defining a captive fluidized bed reactor.

As used herein, the term "riser" reactor (also known as a transport reactor) refers to a zone or vessel (such as, vertical cylindrical pipe) used for net upwards transport of solids (e.g., catalyst particles) in fast-fluidization or pneumatic conveying fluidization regimes. Fast fluidization and pneumatic conveying fluidization regimes are characterized by superficial gas velocities (U) greater than the transport velocity ($U_{tr}$). Fast fluidization and pneumatic conveying fluidization regimes are also described in Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Revised 2nd Edition, Butterworth-Heinemann, Boston, 2010. A fluidized bed reactor, such as a circulating fluidized bed reactor, may be operated as a riser reactor.

As used herein, the term "radiantly heated tubular" or "fired tubes" reactor refers to a furnace and parallel reactor tube(s) positioned within a radiant section of the furnace. The reactor tubes contain a catalytic material (e.g., catalyst particles), which contacts reactant(s) to form a product.

As used herein, the term "convectively heated tubes" reactor refers to a conversion system comprising parallel reactor tube(s) containing a catalytic material and positioned within an enclosure. While any known reactor tube configuration or enclosure may be used, preferably the conversion system comprises multiple parallel reactor tubes within a convective heat transfer enclosure. Preferably, the reactor tubes are straight rather than having a coiled or curved path through the enclosure (although coiled or curved tubes may be used). Additionally, the tubes may have a cross section that is circular, elliptical, rectangular, and/or other known shapes. The tubes are preferentially heated with a turbine exhaust stream produced by a turbine burning fuel gas with a compressed gas comprising oxygen. In other aspects, the reactor tubes are heated by convection with hot gas produced by combustion in a furnace, boiler, or excess air burner. However, heating the reactor tubes with turbine exhaust is preferred because of the co-production of shaft power among other advantages.

As used herein, the term "fixed bed" or "packed bed" reactor refers to a zone or vessel (such as, vertical or horizontal, cylindrical pipe or a spherical vessel) and may include transverse (also known as cross flow), axial flow, and/or radial flow of the gas, where solids (e.g., catalyst particles) are substantially immobilized within the reactor and gas flows such that the superficial velocity (U) is below the velocity required to fluidize the solid particles (i.e., below the minimum fluidization velocity $U_{mf}$) and/or the gas is moving in a downward direction so that solid particle fluidization is not possible.

As used herein, the term "cyclical" refers to a periodic recurring or repeating event that occurs according to a cycle. For example, reactors (e.g., cyclic fixed bed) may be cyclically operated to have a reaction interval, a reheat interval, and/or a regeneration interval.

The duration and/or order of the interval steps may change over time.

As used herein, the term "counter-current" refers to a flow of two streams (e.g., stream (a), stream (b)) in substantially opposing directions. For example, if stream (a) flows from a top portion to a bottom portion of the at least one reaction zone and stream (b) flows from a bottom portion to a top portion of the at least one reaction zone, the flow of stream (a) would be considered counter-current to the flow of stream (b). On a smaller scale within the reaction zone, there may be regions where flow may not be counter-current.

Catalyst Composition

The catalyst composition employed in the present process comprises a microporous crystalline metallosilicate, typically an aluminosilicate, and a Group 10 metal or compound thereof.

Catalyst compositions useful herein include microporous crystalline metallosilicates, such as crystalline aluminosilicates, crystalline ferrosilicates, or other metal containing crystalline silicates (such as those where the metal or metal containing compound is dispersed within the crystalline silicate structure and may or may not be a part of the crystalline framework. Microporous crystalline metallosilicate framework types useful as catalyst compositions herein include, but are not limited to, MWW, MFI, LTL, MOR, BEA, TON, MTW, MTT, FER, MRE, MFS, MEL, DDR, EUO, and FAU.

Particularly suitable microporous metallosilicates for use herein include those of framework type MWW, MFI, LTL, MOR, BEA, TON, MTW, MTT, FER, MRE, MFS, MEL, DDR, EUO, and FAU (such as zeolite beta, mordenite, faujasite, Zeolite L, ZSM-5, ZSM-11, ZSM-22, ZSM-23, ZSM-35, ZSM-48, ZSM-50, ZSM-57, ZSM-58, and MCM-22 family materials) where one or more metals from groups 8, 11 and 13 of the Periodic Table of the Elements (preferably one or more of Fe, Cu, Ag, Au, B, Al, Ga, and or In) are incorporated in the crystal structure during synthesis or impregnated post crystallization. It is recognized that a metallosilicate may have one or more metals present and, for example, a material may be referred to as a ferrosilicate but it will most likely still contain small amounts of aluminum.

The microporous crystalline metallosilicates preferably have a constraint index in the range of about 3 to about 12. Constraint index and a method for its determination are described in U.S. Pat. No. 4,016,218, the entire contents of which are incorporated herein by reference.

Aluminosilicates useful herein having a constraint index of about 3 to about 12 include and are selected from the group consisting of ZSM-5, ZSM-11, ZSM-22, ZSM-23, ZSM-35, ZSM-48, ZSM-50, ZSM-57, ZSM-58, a MCM-22 family material and mixtures of two or more thereof. Preferably, the microporous crystalline aluminosilicate that has a constraint index in the range of about 3 to about 12 is ZSM-5. ZSM-5 is described in U.S. Pat. No. 3,702,886. ZSM-11 is described in U.S. Pat. No. 3,709,979. ZSM-22 is described in U.S. Pat. No. 5,336,478. ZSM-23 is described in U.S. Pat. No. 4,076,842. ZSM-35 is described in U.S. Pat. No. 4,016,245. ZSM-48 is described in U.S. Pat. No. 4,375,573. ZSM-50 is described in U.S. Pat. No. 4,640,829, and ZSM-57 is described in U.S. Pat. No. 4,873,067. ZSM-58 is described in U.S. Pat. No. 4,698,217.

The MCM-22 family material is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30 and mixtures of two or more thereof.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), and ITQ-2 (described in International Patent Publication No. WO 97/17290), MCM-36 (described in U.S. Pat. No. 5,250,277), MCM-49 (described in U.S. Pat. No. 5,236,575), MCM-56 (described in U.S. Pat. No. 5,362,697) and mixtures of two or more thereof. Related zeolites to be included in the MCM-22 family are UZM-8 (described in U.S. Pat. No. 6,756,030) and UZM-8HS (described in U.S. Pat. No. 7,713,513), both of which are also suitable for use as the molecular sieve of the MCM-22 family.

In one or more embodiments, the crystalline metallosilicate has an Si/M molar ratio (where M is a group 8, 11 or 13 metal) greater than about 25, or greater than about 50, or greater than about 100, or greater than 400, or greater than about 1,000, or in the range from about 100 to about 2,000, or from about 100 to about 1,500, or from about 50 to 2,000, or from about 50 to 1,200.

In one or more embodiments, the porous crystalline metallosilicate is crystalline aluminosilicate having a $SiO_2/Al_2O_3$ molar ratio greater than about 25, or greater than about 50, or greater than about 100, or greater than about 400, or greater than about 1,000, or in the range from about 25 to about 2,000, or from about 50 to about 1,500, or from about 100 to about 1,200, or from about 100 to about 1000, or from about 100 to about 500, or from about 100 to about 400.

The Group 10 metal includes, or is selected from the group consisting of nickel, palladium and platinum, preferably platinum. The Group 10 metal content of said catalyst composition is at least 0.005 wt %, based on the weight of the catalyst composition. The Group 10 content is in the range from about 0.005 wt % to about 10 wt %, or from about 0.005 wt % up to about 1.5 wt %, based on the weight of the catalyst composition.

Optionally, the Group 10 metal is present in combination with an additional metal selected from Groups 8, 9, and 11 of the Periodic Table of the Elements and the rare earth metals, such as Ga, In, Zn, Cu, Re, Mo, W, La, Fe, Ag, Pd, Rh, Pr, La, and/or oxides, sulfides, nitrides, and/or carbides of these metals. Alternatively or additionally, the Group 10 metal is present in combination with a Group I alkali metal and/or a Group 2 alkaline earth metal.

A preferred Group 9 metal is Rh, which may form an alloy with the Group 10 metal. Preferably, the molar ratio of Rh to Group 10 metal is in the range from about 0.1 to about 5.

Typically, the rare earth metal is selected from the group consisting of yttrium, lanthanum, cerium, praseodymium, and mixtures or combinations thereof. Preferably, the molar ratio of rare earth metal to Group 10 metal is in the range from about 1 to about 10. The rare earth metal may be added to the catalyst composition during or after synthesis of the microporous crystalline molecular sieve as any suitable rare earth metal compound.

Preferred additional metals are Group 11 metals. Typically, the Group 11 metal is selected from the group consisting of Cu, Ag, Au, and mixtures of two or more thereof; preferably Cu or Ag. The Group 11 metal content of the catalyst composition is such that the molar ratio of Group 11 metal to Group 10 metal is at least 0.01, based on the molar quantities of each in the catalyst composition. Preferably, the molar ratio of Group 11 metal to Group 10 metal is in the range from about 0.1 to 10 or from about 0.5 to 5 based on the molar quantities of each in the catalyst composition. The Group 11 metal may be added to the catalyst composition during or after synthesis of the microporous crystalline molecular sieve as any suitable Group 11 metal compound.

In one or more embodiments, the catalyst composition has an Alpha Value (as measured prior to the addition of the Group 10 metal, preferably platinum) of less than about 25, preferably of less than about 15.

Generally, the Group 1 alkali metal and/or the Group 2 alkaline earth metal is present as an oxide. The Group 1 alkali metal includes, or is selected from the group consisting of lithium, sodium, potassium, rubidium, caesium, and mixtures of two or more thereof, preferably sodium. The Group 2 alkaline earth metal, includes, or is selected from the group consisting of beryllium, magnesium, calcium, strontium, barium, and mixtures of two or more thereof.

In one or more embodiments, the molar ratio of said Group 1 alkali metal to Al is at least about 0.5, or at least about 1, or in the from at least about 1 up to about 3, preferably at least about 2, more preferably at least about 3. In one or more embodiments, the molar ratio of said Group 2 alkaline earth metal to Al is at least about 0.5, or at least about 1, or from at least about 1 up to about 3, preferably at least about 2, more preferably at least about 3.

Useful catalyst compositions comprise a crystalline aluminosilicate, which is optionally combined with one, two, or more additional metals or metal compounds. Preferred combinations include: platinum on MFI silversilicate, platinum on coppersilicate MFI, platinum with silver on ZSM-5, and platinum with copper on ZSM-5.

The catalyst compositions of this invention can be combined with a matrix or binder material to render them attrition resistant and more resistant to the severity of the conditions to which they will be exposed during use in hydrocarbon conversion applications. Preferred binder materials comprise one or more of silica, titania, zirconia, metal silicates of Group 1 or Group 13 of the Periodic Table, carbides, nitrides, aluminum phosphate, aluminum molybdate, aluminate, surface passivated alumina, and mixtures thereof. Preferably, suitable binder materials have a lower affinity for Group 10 metal particles, e.g. Pt, in comparison with the crystalline metallosilicate, e.g. aluminosilicate. The combined compositions can contain 1 wt % to 99 wt % of the materials of the invention based on the combined weight of the matrix (binder) and material of the invention. The relative proportions of microporous crystalline material and matrix may vary widely, with the crystal content ranging from about 1 wt % to about 90 wt % and more usually, particularly when the composite is prepared in the form of beads, in the range of about 2 wt % to about 80 wt % of the composite.

The formulated catalyst composition may be made into one or more forms. For example, the formulated catalyst can be extruded to form an extrudate, particularly into a shaped extrudate having a geometric form. Also, the formulated catalyst composition may be made into a particle, such as, for example, a spray dried particle, an oil drop particle, a mulled particle, or a spherical particle. The formulated catalyst composition may be made into a slurry.

The catalyst compositions can be made by the methods according to the Examples, below.

Feedstock

Feedstock useful herein generally comprises acyclic hydrocarbons, preferably acyclic $C_2$-$C_{10}$ hydrocarbons. Acyclic $C_2$-$C_{10}$ hydrocarbons include, but are not limited to alkanes (e.g., ethane, propane, butane, pentane, hexane, etc.), alkenes (e.g., ethylene, propylene, butylene, etc.), alkynes (e.g., ethyne, propyne, 1-butyne, 2-butyne, etc.), dialkenes (e.g., 1,2-propadiene, 1,3-butadiene, 1,3-pentadiene, etc.) and combinations thereof. An acyclic $C_2$-$C_{10}$ hydrocarbon feedstock, useful herein, is obtainable from crude oil or natural gas condensate.

In various aspects, the feedstock may preferably be an acyclic $C_5$ feedstock and can include cracked $C_5$ (in various degrees of unsaturation: alkenes, dialkenes, alkynes) produced by refining and chemical processes, such as fluid catalytic cracking (FCC), reforming, hydrocracking, hydrotreating, coking, and steam cracking.

In one or more embodiments, the acyclic $C_5$ feedstock useful in the process of this invention comprises pentane, pentene, pentadiene and mixtures of two or more thereof. Preferably, in one or more embodiments, the acyclic $C_5$ feedstock comprises at least about 50 wt %, or 60 wt %, or 75 wt %, or 90 wt % n-pentane, or in the range from about 50 wt % to about 100 wt % n-pentane.

The acyclic $C_5$ hydrocarbon feedstock optionally does not comprise $C_6$ aromatic compounds, such as benzene. Preferably $C_6$ aromatic compounds are present at less than 5 wt %, preferably less than 1 wt %, preferably less than 0.01 wt %, and preferably at zero wt %.

Additionally or alternatively, the acyclic $C_5$ hydrocarbon feedstock optionally does not comprise benzene, toluene, or xylene (ortho, meta, or para). Preferably, any benzene, toluene, or xylene (ortho, meta, or para) compounds are present at less than 5 wt %, preferably less than 1 wt %, preferably less than 0.01 wt %, and preferably at zero wt %.

The acyclic $C_5$ hydrocarbon feedstock optionally does not comprise $C_{6+}$ aromatic compounds. Preferably $C_{6+}$ aromatic compounds are present at less than 5 wt %, preferably less than 1 wt %, preferably less than 0.01 wt %, and preferably at zero wt %.

Hydrocarbon Conversion Processes

In any embodiment, the catalyst rejuvenation processes of this disclosure are generally employed in hydrocarbon conversion processes that comprise contacting a hydrocarbon feedstock with any one of the aforementioned catalyst compositions in at least one reaction zone to form a hydrocarbon reaction product. Examples of suitable hydrocarbon conversion processes include: the conversion of acyclic $C_5$ hydrocarbons to cyclic $C_5$ hydrocarbons; the conversion of acyclic $C_{6+}$ hydrocarbons to aromatic $C_{6+}$ hydrocarbons; the conversion of $C_2$-$C_5$ hydrocarbons to $C_{6+}$ aromatics; and/or the dehydrogenation of paraffins to olefins and/or dienes.

In any embodiment, suitable hydrocarbon conversion processes can be conducted in a wide range of reactor configurations. Particularly preferred reactor configurations include convectively heated tubes (as described in U.S. Ser. No. 62/250,674, filed Nov. 4, 2015); fired tubes (as described in U.S. Ser. No. 62/250,693, filed Nov. 4, 2015); a riser reactor (as described in U.S. Ser. No. 62/250,682, filed Nov. 4, 2015); a circulating fluidized bed or a circulating settling bed with counter-current flow (as described in U.S. Ser. No. 62/250,680, filed Nov. 4, 2015); a cyclic fluidized bed reactor or a cyclic fixed bed reactor (as described in U.S. Ser. No. 62/250,677, filed Nov. 4, 2015); and/or an electrically heated reactor. In addition, suitable hydrocarbon conversion processes can be conducted in a single reaction zone or in a plurality of reaction zones, such as an adiabatic reaction zone followed by a diabatic reaction zone (as described in U.S. Ser. No. 62/250,697, filed Nov. 4, 2015).

Acyclic $C_5$ Conversion Process

A particularly preferred hydrocarbon conversion process is the conversion of acyclic $C_5$ hydrocarbons to cyclic $C_5$ hydrocarbons, the process comprising the steps of contacting said feedstock and, optionally, hydrogen under acyclic $C_5$ conversion conditions in the presence of any one of the aforementioned catalyst compositions to form said hydrocarbon reaction product.

Typically, the acyclic $C_5$ hydrocarbon(s) contained in the $C_5$ feedstock is fed into a first reactor loaded with a catalyst, where the acyclic $C_5$ hydrocarbons contact the catalyst under conversion conditions, whereupon at least a portion of the acyclic $C_5$ hydrocarbon(s) molecules are converted into cyclopentadiene (CPD) molecules, and a reaction product containing CPD and, optionally, other cyclic hydrocarbons (e.g., $C_5$ cyclic hydrocarbons such as cyclopentane and cyclopentene) exits the first reactor as a first reactor hydrocarbon effluent. Preferably, a hydrogen co-feedstock comprising hydrogen and, optionally, light hydrocarbons, such as $C_1$-$C_4$ hydrocarbons, is also fed into the first reactor (as described in U.S. Ser. No. 62/250,702, filed Nov. 4, 2015). Preferably, at least a portion of the hydrogen co-feedstock is admixed with the $C_5$ feedstock prior to being fed into the first reactor. The presence of hydrogen in the feed mixture at the inlet location, where the feed first comes into contact with the catalyst, prevents or reduces the formation of coke on the catalyst particles.

The product of the process for conversion of an acyclic $C_5$ feedstock comprises cyclic $C_5$ compounds. The cyclic $C_5$ compounds comprise one or more of cyclopentane, cyclopentene, cyclopentadiene, and includes mixtures thereof. The cyclic $C_5$ compounds comprise at least about 20 wt %, or 30 wt %, or 40 wt %, or 50 wt % cyclopentadiene, or in the range of from about 10 wt % to about 80 wt %, alternately 20 wt % to 70 wt % of cyclopentadiene.

The acyclic $C_5$ conversion conditions include at least a temperature, a partial pressure, and a weight hourly space velocity (WHSV). The temperature is in the range of about 400° C. to 700° C., or about 450° C. to about 800° C., or in the range from about 500° C. to about 650° C., preferably, in the range from about 500° C. to about 600° C.

The partial pressure is in the range of about 3 psia to about 100 psia at the reactor inlet (21 to 689 kPa-a), or in the range from about 3 psia to about 50 psia (21 to 345 kPa-a), preferably, in the range from about 3 psia to about 20 psia (21 to 138 kPa-a). The weight hourly space velocity is in the range from about 1 $hr^{-1}$ to about 50 $hr^{-1}$, or in the range from about 1 hr to about 20 $hr^{-1}$. Such conditions include a molar ratio of the optional hydrogen co-feed to the acyclic $C_5$ hydrocarbon in the range of about 0 to 3 (e.g., 0.01 to 3.0), or in the range from about 0.5 to about 2. Such conditions may also include co-feed $C_1$-$C_4$ hydrocarbons with the acyclic $C_5$ feed.

In any embodiment, this invention relates to a process for conversion of n-pentane to cyclopentadiene comprising the steps of contacting n-pentane and, optionally, hydrogen (if present, typically $H_2$ is present at a molar ratio of hydrogen to n-pentane of 0.01 to 3.0) with one or more catalyst compositions, including but not limited to the catalyst compositions described herein, to form cyclopentadiene at a temperature of 400° C. to 700° C., a partial pressure of 3 psia to about 100 psia at the reactor inlet (21 to 689 kPa-a), and a weight hourly space velocity of 1 $hr^{-1}$ to about 50 $hr^{-1}$.

The use of the catalyst compositions of this invention provides a conversion of at least about 10%, or at least about 20%, or at least about 30%, or in the range of from about 20% to about 50%, of said acyclic $C_5$ feedstock under acyclic $C_5$ conversion conditions of an n-pentane containing feedstock with equimolar $H_2$, a temperature in the range of from 400° C. to about 500° C., or about 450° C., an n-pentane partial pressure of about 5 psia (35 kPa-a), or about 7 psia (48 kPa-a), or from about 4 psia to about 6 psia at the reactor inlet (28 to 41 kPa-a), and an n-pentane weight hourly space velocity of about 2 $hr^{-1}$, or between 1 $hr^{-1}$ and 5 $hr^{-1}$.

The use of any one of the catalyst compositions of this invention provides a carbon selectivity to cyclic $C_5$ compounds of at least about 10%, or at least about 20%, or at least about 30%, or in the range from about 20% to about 50%, under acyclic $C_5$ conversion conditions including an n-pentane feedstock with equimolar $H_2$, a temperature in the range of about 400° C. to about 500° C., or about 450° C., an n-pentane partial pressure between 3 psia and 10 psia (21 to 69 kPa-a), and an n-pentane weight hourly space velocity between 10 $hr^{-1}$ and 20 $hr^{-1}$.

The use of any one of the catalyst compositions of this invention provides a carbon selectivity to cyclopentadiene of at least about 20%, or at least about 30%, or at least about 40%, or at least about 50%, or in the range from about 30% to about 50%, under acyclic $C_5$ conversion conditions including an n-pentane feedstock with equimolar $H_2$, a temperature in the range of about 550° C. to about 600° C., an n-pentane partial pressure of about 7 psia (48 kPa-a), or about 5 psia (35 kPa-a), or from about 4 psia to about 6 psia (28 to 41 kPa-a), and an n-pentane weight hourly space velocity of about 2 $hr^{-1}$, or between 1 $hr^{-1}$ and 5 $hr^{-1}$.

In the presence of the catalyst, a number of desired and undesirable side reactions may take place. The net effect of the reactions is the production of hydrogen and the increase of total volume (assuming constant total pressure). One particularly desired overall reaction (i.e., intermediate reaction steps are not shown) is:

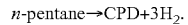
n-pentane→CPD+3H$_2$.

Additional overall reactions include, but are not limited to:

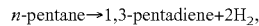
n-pentane→1,3-pentadiene+2H$_2$,

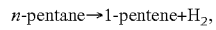
n-pentane→1-pentene+H$_2$,

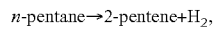
n-pentane→2-pentene+H$_2$,

n-pentane→2-methyl-2-butene+H$_2$,

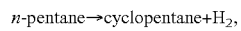
n-pentane→cyclopentane+H$_2$,

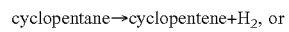
cyclopentane→cyclopentene+H$_2$, or

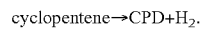
cyclopentene→CPD+H$_2$.

Fluids inside the first reactor are essentially in gas phase. At the outlet of the first reactor, a first reactor hydrocarbon effluent, preferably in gas phase, is obtained. The first reactor hydrocarbon effluent may comprise a mixture of the following hydrocarbons, among others: heavy components comprising more than 8 carbon atoms such as multiple-ring aromatics; $C_8$, $C_7$, and $C_6$ hydrocarbons such as one-ring aromatics; CPD (the desired product); unreacted $C_5$ feedstock material such as n-pentane; $C_5$ by-products such as pentenes (1-pentene, 2-pentene, e.g.), pentadienes (1,3-pentadiene; 1,4-pentadiene, e.g.), cyclopentane, cyclopentene, 2-methylbutane, 2-methyl-1-butene, 3-methyl-1-butene, 2-methyl-1,3-butadiene, 2,2-dimethylpropane, and the like; $C_4$ by-products such as butane, 1-butene, 2-butene, 1,3-butadiene, 2-methylpropane, 2-methyl-1-propene, and the like; $C_3$ by-products such as propane, propene, and the like; $C_2$ by-products such as ethane and ethene, methane, and hydrogen.

The first reactor hydrocarbon effluent may comprise CPD at a concentration of C(CPD)1 wt %, based on the total weight of the $C_5$ hydrocarbons in the first reactor hydrocarbon effluent; and a1≤C(CPD)1≤a2, where a1 and a2 can be, independently, 15, 16, 18, 20, 22, 24, 25, 26, 28, 30, 32, 34, 35, 36, 38, 40, 45, 50, 55, 60, 65, 70, 75, 80, or 85 as long as a1<a2.

The first reactor hydrocarbon effluent may comprise acyclic diolefins at a total concentration of C(ADO)1 wt %, based on the total weight of the $C_5$ hydrocarbons in the first reactor hydrocarbon effluent; and b1≤C(ADO)1≤b2, where b1 and b2 can be, independently, 20, 18, 16, 15, 14, 12, 10, 8, 6, 5, 4, 3, 2, 1, or 0.5, as long as b1≤b2. Preferably, 0.5≤C(ADO)≤10.

As a result of the use of the catalyst and the choice of reaction conditions in the first reactor, a high CPD to acyclic diolefin molar ratio in the first reactor hydrocarbon effluent can be achieved such that C(CPD)1/C(ADO)1≥1.5, preferably 1.6, 1.8, 2.0, 2.2, 2.4, 2.5, 2.6, 2.8, 3.0, 3.2, 3.4, 3.5, 3.6, 3.8, 4.0, 5.0, 6.0, 8.0, 10, 12, 14, 15, 16, 18, or 20. The high ratio of C(CPD)1/C(ADO)1 significantly reduces CPD loss as a result of Diels-Alder reactions between CPD and acyclic dienes in subsequent processing steps, and therefore, allows the processes of the present invention to achieve high DCPD yield and high DCPD purity for the subsequently produced DCPD fractions.

Desirably, the total absolute pressure and temperature of the first reactor hydrocarbon effluent should be maintained at levels such that the dimerization of CPD to form DCPD is substantially avoided, and the Diels-Alder reactions between CPD and acyclic dienes are substantially inhibited.

Because the overall conversion from acyclic $C_5$ hydrocarbons to CPD and hydrogen results in substantial volume increase (assuming constant total system pressure), a low partial pressure of CPD and/or a low partial pressure of hydrogen in the reaction mixture favors the conversion of acyclic $C_5$ hydrocarbons. The total partial pressure of $C_5$ hydrocarbons and hydrogen in the first reactor effluent at the outlet is desired to be lower than atmospheric pressure. Thus, where insufficient co-feedstock of a $C_1$-$C_4$ hydrocarbon or other co-feedstock is introduced into the first reactor, the total overall pressure of the first reactor effluent is desirably sub-atmospheric, in order to achieve a level of satisfactory conversion from acyclic $C_5$ hydrocarbons to CPD. However, direct separation of a sub-atmospheric stream has the disadvantage of potential oxygen/air ingress into the system, resulting in oxidation of CPD and other hydrocarbons and formation of undesirable species in the system. Thus, it is desirable that the first reactor hydrocarbon effluent is processed to a higher total pressure before separation thereof. Eductor systems, can be used for that purpose (as described in U.S. Ser. No. 62/250,708, filed Nov. 4, 2015).

Catalyst Rejuvenation

Over the course of the hydrocarbon conversion processes described herein, the activity of the catalyst generally gradually declines to form a deactivated catalyst due to the accumulation of carbonaceous or coke material and/or agglomeration of metal on the catalyst material during the reaction. It has presently been discovered that deactivation due to metal agglomeration occurs at a slower rate than deactivation due to coke formation during the course of the hydrocarbon conversion processes. As such, a rejuvenation cycle is advantageously performed to produce a rejuvenated catalyst having restored or substantially restored catalyst activity, typically by removing at least a portion of the incrementally deposited coke material from the catalyst composition. Preferably, rejuvenated catalyst has activity restored to at least 50% of the activity of the catalyst prior to deactivation, more preferably at least 60%, more preferably at least 80%. Rejuvenated catalyst also preferably has restored or substantially restored catalyst selectivity, e.g., selectivity restored to at least 50% of the selectivity of the catalyst prior to deactivation, more preferably at least 60%, more preferably at least 80%. As used herein, "incrementally deposited coke" refers to the amount of coke that is deposited on the catalyst during a conversion cycle. Typically, a rejuvenation cycle is employed when the catalyst composition comprises >1 wt % incrementally deposited coke, such as >5 wt % incrementally deposited coke, or >10 wt % incrementally deposited coke.

Rejuvenation is carried out in at least one rejuvenation zone. The rejuvenation zone(s) may be located in situ in the reaction zone or ex situ in one or more rejuvenation zones apart from the reaction zone. Typically, in situ rejuvenation methods are employed when the reactor configuration of the hydrocarbon conversion process is a fixed bed system, such as a heated tubular reactor or other type of fixed bed reactor. Typically, rejuvenation is carried out in a separate rejuvenation zone when the reactor configuration of the hydrocarbon conversion process is a moving bed system, e.g., a circulating fluidized bed or a circulating settling bed.

A typical rejuvenation cycle begins by discontinuing contact of the hydrocarbon feedstock with the catalyst composition in the reaction zone or by transfer of the catalyst composition to a separate rejuvenation zone. Often, combustible hydrocarbon gas, including feedstock or hydrocarbon reaction product, is purged from the catalyst composition using a purge gas, for example, $N_2$. This purge step may typically be omitted if $CO_2$ is employed as the oxidant during the mild oxidation step. Optionally, the purging step may be proceeded by a step of contacting the catalyst with a $H_2$ containing stream for partial, reductive removal of coke. The following rejuvenation steps, including at least mild oxidation, are then performed.

Rejuvenation of the catalyst material in the at least one rejuvenation zone may occur as a continuous process or may be done batch wise. Preferably, a rejuvenation cycle is periodically performed after beginning the specified hydrocarbon conversion process. A rejuvenation cycle may be advantageously performed ≥10 minutes, e.g., ≥30 minutes, ≥2 hours, ≥5 hours, ≥24 hours, ≥2 days, ≥5 days, ≥20 days, after beginning the specified hydrocarbon conversion process or since the previous rejuvenation cycle.

In any embodiment, rejuvenation of the catalyst comprises a mild oxidation step comprising contacting the catalyst composition with an oxygen-containing gaseous stream under conditions effective to remove at least a portion of incrementally deposited coke material on the catalyst. Typically, these conditions include a temperature range of about 250° C. to about 500° C., and a total pressure of about 0.1 bar to about 100 bar, preferably at or about atmospheric pressure. Further, the oxygen-containing gaseous stream is typically supplied to the rejuvenation zone(s) at a total WHSV in the range from about 1 to about 10,000. The source of oxygen may be, for example, $O_2$, $O_3$, nitrogen oxides, $CO_2$, and mixtures or combinations of any of the foregoing. Where the oxygen source is selected from $O_2$, $O_3$, and/or nitrogen oxides, the concentration of oxygen in the gaseous stream is typically in the range from about 0.1 to about 20% by volume, preferably from about 0.5 to about 5%. Alternatively, where $CO_2$ is utilized as the oxygen source, higher oxygen concentrations may be utilized, e.g., up to 100% $CO_2$. Additionally, where $CO_2$ is utilized as the oxygen source, lower levels of the other oxidants (i.e., $O_2$, $O_3$, and/or nitrogen oxides) may be utilized sequentially with the $CO_2$ and/or blended into the $CO_2$ In any embodiment, the oxygen-containing gaseous stream may further comprise a non-reactive substance (e.g., $N_2$, CO).

It has been found that the preferred mild oxidation temperature range for restoring or substantially restoring catalyst activity and selectivity depends at least in part on the metal component(s) of the catalyst composition. For example, the preferred mild oxidation temperature range of a catalyst composition comprising a Group 10 metal in combination with a rare earth metal typically ranges up to about 500° C., such as from about 400° C. to about 500° C. Alternatively, the preferred mild oxidation temperature range of a catalyst composition comprising a Group 10 metal in combination with a Group 11 metal typically ranges up to about 375° C., such as from about 300° C. to about 350° C. Alternatively, the catalyst composition may exhibit restored or substantially restored activity and selectivity over a wide range of mild oxidation temperatures, such as aspects where the Group 10 metal is present in the absence of additional metals, for example, where the metal component of the catalyst composition consists essentially of or consists of the Group 10 metal.

The mild oxidation step typically has a time duration of ≤300 mins, ≤240 mins, ≤90 mins, e.g., ≤60 mins, ≤30 mins, ≤10 mins, such as ≤1 min, or ≤10 seconds. Advantageously, the conditions are adjusted over the time duration of the mild oxidation step to minimize the local temperature in the vicinity of the noble metal while maximizing coke removal. Particularly, the mild oxidation step is preferably conducted under an initial set of conditions effective to remove less refractory coke. For example, suitable initial conditions include a low temperature, a low oxygen concentration and/or partial pressure in the gaseous stream, and/or utilization of a low activity oxidant as the oxygen source, e.g., $CO_2$. Preferably, the conditions are subsequently adjusted over the time duration of the rejuvenation to those effective to remove highly refractive coke. For example, adjusting the conditions may be achieved via increasing the operating temperature, increasing the oxygen concentration and/or partial pressure in the gaseous stream, and/or exchanging the oxygen source for a higher activity oxidant, e.g., nitrogen oxides, $O_2$, $O_3$, or mixtures thereof.

Following the mild oxidation, purge gas is generally reintroduced to purge oxidants from the catalyst composition using a purge gas, for example, $N_2$. This purging step may be omitted if $CO_2$ is the oxidant as it will not produce a flammable mixture.

Typically, rejuvenation further comprises one or more hydrogen treatment steps. Generally, each hydrogen treatment step comprises contacting the catalyst composition with a hydrogen-containing gaseous stream at a temperature ranging from about 200° C. to about 800° C. at a total pressure of up to about 100 bar. In any embodiment, the hydrogen-containing gaseous stream comprises ≥10 vol % $H_2$, such as ≥50 vol %, ≥70 vol %, preferably ≥90 vol % $H_2$.

Often, at least one hydrogen treatment is an optional pretreatment step performed prior to the mild oxidation. The optional pretreatment step is generally conducted under conditions effective to remove at least a portion of incrementally deposited coke material on the catalyst, thereby forming an at least partially rejuvenated catalyst material and a volatile hydrocarbon, such as, but not limited to methane. For example, the pretreatment can be conducted at temperatures ranging from about 400° C. to about 800° C., preferably from about 500° C. to about 600° C.; at pressures ranging from about 1 to about 100 bar, preferably from about 5 to about 20 bar; and $H_2$ concentrations of ≥10 vol % $H_2$, such as ≥50 vol %, ≥70 vol %, preferably ≥90 vol % $H_2$. Without wishing to be bound by theory, it is believed that this optional pretreatment step may reduce the overall exotherm during the subsequent oxidative coke burn, therefore limiting agglomeration of the Group 10 metal particles. Typically, the mild oxidation step, in conjunction with the optional pretreatment step, is effective at removing at least 10 wt % (≥10 wt %) of incrementally deposited coke material. Between about 10 wt % to about 100 wt %, preferably between about 90 wt % to about 100 wt % of incrementally deposited coke material is removed.

Additionally or alternatively, at least one hydrogen treatment is generally performed subsequent to the mild oxidation. The subsequent hydrogen treatment is generally conducted under conditions effective to convert the noble metal oxide formed during mild oxidation to the elemental metal. For example, reduction can be performed at temperatures ranging from about 200° C. to about 800° C., preferably from about 300° C. to about 500° C.; at pressures ranging from about 1 to about 100 bar, preferably from about 1 to about 5 bar; and $H_2$ concentrations of ≥10 vol % $H_2$, such as ≥50 vol %, ≥70 vol %, preferably ≥90 vol % $H_2$.

Following purging and the optional subsequent hydrogen treatment, the rejuvenation cycle is complete and flow of hydrocarbon feedstock may be resumed for fixed bed systems or the catalyst transferred back to the reaction zone for moving bed systems.

Catalyst Regeneration

The hydrocarbon conversion processes may further comprise periodically performing one or more regeneration cycles to remove carbonaceous or coke material on the catalyst composition that is not removed by rejuvenation.

A regeneration cycle may be advantageously performed between about once every 6 days to about once every 180 days, preferably between about once every 10 days to about once every 40 days after beginning the specified hydrocarbon conversion process.

Advantageously, performing a rejuvenation cycle lengthens the amount of time the catalyst can maintain adequate activity before the next regeneration cycle. Accordingly, the hydrocarbon conversion processes may comprise ≥1, e.g., ≥2, ≥5 or ≥20 rejuvenation cycles between each regeneration cycle.

A typical regeneration cycle begins by discontinuing contact of the hydrocarbon feedstock with the catalyst composition in the reaction zone. Often, combustible hydrocarbon gas, including feedstock or reactor product, is purged from the catalyst composition using a purge gas, for example, $N_2$. The following regeneration steps are then performed either in situ in the reaction zone or in one or more separate regeneration zones apart from the reaction zone.

In any embodiment, regeneration of the catalyst is preferably achieved by a coke removal step comprising contacting the catalyst composition with an oxygen-containing gaseous stream under conditions effective to remove at least a portion of coke material on the catalyst, followed by an oxychlorination step comprising contacting the catalyst composition with a gaseous stream comprising a chlorine source and an oxygen source under conditions effective for dispersing Group 10 metal particles on the surface of the catalyst and forming a first Group 10 metal chlorohydrate, followed by chlorine stripping step comprising contacting the catalyst composition with a gaseous stream comprising an oxygen source, and optionally a chlorine source, under conditions effective for increasing the O/Cl ratio of the first Group 10 metal chlorohydrate to produce a second Group 10 metal chlorohydrate. Generally, regeneration further comprises a reduction step, and optionally a sulfidation step. Typically, at least 10 wt % (≥10 wt %) of total coke material on the catalyst composition (i.e., not limited to incrementally deposited coke) present at the start of regeneration is removed. For example, between about 10 wt % to about 100 wt %, preferably between about 90 wt % to about 100 wt % of coke material is removed.

Following regeneration, purge gas is generally reintroduced to purge oxidant gas from the catalyst composition using a purge gas, for example, $N_2$. The catalyst may then be reduced, for example, using $H_2$, and optionally sulfided. Subsequently, the regeneration cycle is complete and flow of hydrocarbon feedstock may be or the catalyst transferred back to the reaction zone. Regeneration requires less than about 10 days, preferably less than about 3 days to complete.

Products and Articles

The process for producing cyclic $C_5$ compounds of this invention comprises one or more cyclic $C_5$ compositions. Such composition comprises one or more cyclic $C_5$ compounds. These cyclic $C_5$ compounds include and are selected from the group consisting of cyclopentadiene, dicyclopentadiene, cyclopentene, cyclopentane, pentene, pentadiene, and mixtures of two or more thereof.

The cyclic $C_5$ compounds may be reacted with a substrate to form a product. In some embodiments, the substrate comprise a double bond. Such product includes is one or more of a Diels Alder reaction derivative of cyclopentadiene, cyclic olefin copolymers, cyclic olefin polymers, polycyclopentene, ethylidene norbornene, EPDM rubber, alcohols, plasticizers, blowing agents, solvents, octane enhancers, gasoline, unsaturated polyester resins, hydrocarbon resin tackifiers, formulated epoxy resins, polydicyclopentadiene, metathesis polymers of norbornene or substituted norbornenes or dicyclopentadiene, tetracyclodocene, or any combination of two or more thereof. The Diels Alder reaction derivatives of cyclopentadiene is or comprises norbornene or substituted norbornenes.

The product may be made into a useful article. Such article comprise any of the products made or derived from the process of this invention. Particularly, the article may be one or more of wind turbine blades, composites containing glass or carbon fibers, and formulated adhesives.

The following examples illustrate the present invention. Numerous modifications and variations are possible and it is to be understood that within the scope of the appended claims, the invention may be practiced otherwise than as specifically described herein.

EXAMPLES

Example 1—ZSM-5/Pt/Ag Catalyst Composition Synthesis (Catalyst A)

A synthesis mixture with ~22% solids was prepared from 8,800 g of deionized (DI) water, 600 g of 50% NaOH solution, 26 g of 43% Sodium Aluminate solution, 730 g of n-propyl amine 100% solution, 20 g of ZSM-5 seed crystals, and 3,190 g of Sipernat™ 340 specialty silica were mixed in a 5-gal pail container and then charged into a 5-gal autoclave after mixing. The synthesis mixture had the following molar composition:

| | |
|---|---|
| $SiO_2/Al_2O_3$ | ~470 |
| $H_2O/SiO_2$ | ~10.7 |
| $OH/SiO_2$ | ~0.16 |
| $Na/SiO_2$ | ~0.16 |
| n-PA/Si | ~0.25. |

The synthesis mixture was mixed and reacted at 210° F. (99° C.) at 350 rpm for 72 hours. The resulting reaction slurry was discharged and stored in a 5-gal pail container. The XRD pattern of the as-synthesized support material showed the typical pure phase of ZSM-5 topology. The SEM of the as-synthesized support material showed that the material was composed of a mixture of crystals with size of ~0.5-1 micron. The resulting ZSM-5 crystals had a $SiO_2/Al_2O_3$ molar ratio of ~467, and a sodium content of ~0.25 wt %.

The synthesized support material was calcined for 6 hours in nitrogen at 900° F. (482° C.). After cooling, the sample was re-heated to 900° F. (482° C.) in nitrogen and held for three hours. The atmosphere was then gradually changed to 1.1, 2.1, 4.2, and 8.4% oxygen in four stepwise increments. Each step was held for 30 minutes. The temperature was increased to 1000° F. (540° C.), the oxygen content was increased to 16.8%, and the material was held at 1000° F. (540° C.) for 6 hours. After cooling, ~0.29 wt % Ag was added via incipient wetness impregnation using an aqueous solution of silver nitrate. The Ag impregnated catalyst was dried at 250° F. (121° C.) for four hours. Subsequently, ~0.44 wt % Pt was added via incipient wetness impregnation using an aqueous solution of tetraamine platinum hydroxide. The resulting catalyst composition (Catalyst A) was dried at 250° F. (121° C.) overnight, and lastly calcined in air at 610° F. (321° C.) for 1 hour.

Example 2—ZSM-5/$SiO_2$(65:35)/Cu/Pt (3:1) Catalyst Composition Synthesis (Catalyst B)

A sample of the zeolite support material synthesized in Example 1 was used to prepare a 65 wt % zeolite/35 wt % silica particle in accordance with the following procedure. First, 65 parts by weight of the synthesized zeolite support material of Example 1 in sodium form was mulled with 35 parts by weight of silica. The silica was equally supplied by Ultrasil PM™ modified silica and by Ludox™ HS-40 colloidal silica. Water was then added in an amount sufficient to produce a mull mixture comprising ~62.5 wt % solids. The mull mixture was extruded into 1/16" (0.16 cm) cylinders. After drying, the extrudate material was heated to 900° F. (482° C.) in nitrogen and held for three hours. The atmosphere was then gradually changed to 1.1, 2.1, 4.2, and 8.4% oxygen in four stepwise increments. Each step was held for 30 minutes. The temperature was increased to 1000° F. (540° C.), the oxygen content was increased to 16.8%, and the material was held at 1000° F. (540° C.) for 6 hours. After cooling, 120 g of the calcined extrudate was sequentially impregnated with Cu and Pt. First, ~0.28 wt % Cu was added via incipient wetness impregnation using an aqueous solution of copper (II) nitrate hydrate in an amount sufficient to target a final copper to platinum molar ratio of 3:1. The Cu impregnated catalyst was dried at 250° F. (121° C.) for 4 hours. Subsequently, ~0.325 wt % Pt was added via incipient wetness impregnation using tetraamine platinum nitrate. The resulting catalyst composition (Catalyst B) was dried in air at room temperature overnight and then at 250° F. (121° C.) for 2.5 hours and lastly calcined in air at 660° F. (349° C.) for 3 hours. Analysis demonstrated that the synthesized Catalyst B composition contained some sulfur content (~400 ppm).

Example 3—ZSM-5/Cu/Pt (6:1) Catalyst Composition Synthesis (Catalyst C)

A sample of the zeolite support material synthesized in Example 1 in sodium form was calcined for 6 hours in nitrogen at 900° F. (482° C.). After cooling, the sample was re-heated to 900° F. (482° C.) in nitrogen and held for 3 hours. The atmosphere was then gradually changed to 1.1, 2.1, 4.2, and 8.4% oxygen in four stepwise increments. Each step was held for 30 minutes. The temperature was increased to 1000° F. (540° C.), the oxygen content was increased to 16.8%, and the material was held at 1000° F. (540° C.) for 6 hours. After cooling, 20 g of the calcined support material was sequentially impregnated with Cu and Pt. First, ~0.89 wt % Cu was added via incipient wetness impregnation using an aqueous solution of copper (II) nitrate hydrate. The Cu impregnated catalyst was dried at 250° F. (121° C.) for 4 hours. Subsequently, 0.58 wt % Pt was added via incipient wetness impregnation using an aqueous solution of tetraamine platinum nitrate (for a final copper to platinum molar ratio of 6:1). The resulting catalyst composition (Catalyst C) was dried at 250° F. (121° C.) for 5 days, and lastly calcined in air at 610° F. (321° C.) for 1 hour.

Example 4—ZSM-5/Pt/Ag Catalyst Composition Synthesis (Catalyst D)

A synthesis mixture with ~22% solids was prepared from 8,800 g of deionized (DI) water, 600 g of 50% NaOH solution, 26 g of 45% Sodium Aluminate solution, 730 g of n-propyl amine 100% solution, 40 g of ZSM-5 seed crystals, and 3,190 g of Ultrasil PM™ modified silica were mixed in a 5-gal pail container and then charged into a 5-gal autoclave after mixing. The synthesis mixture had the following molar composition:

| | |
|---|---|
| $SiO_2/Al_2O_3$ | ~470 |
| $H_2O/SiO_2$ | ~12.1 |
| $OH/SiO_2$ | ~0.16 |
| $Na/SiO_2$ | ~0.16 |
| n-PA/Si | ~0.25. |

The synthesis mixture was mixed and reacted at 230° F. (110° C.) at 250 rpm for 72 hours. The resulting reaction slurry was discharged and stored in a 5-gal pail container. The XRD pattern of the as-synthesized support material showed the typical pure phase of ZSM-5 topology. The SEM of the as-synthesized support material showed that the material was composed of a mixture of large crystals with size of ~1-2 micron. The resulting ZSM-5 crystals had a $SiO_2/Al_2O_3$ molar ratio of ~400, total surface area (SA)/ (micropore SA+mesopore SA) of 468 (422+45) m$^2$/g, and a sodium content of ~0.37 wt %.

The synthesized support material was calcined for 6 hours in nitrogen at 900° F. (482° C.). After cooling, the sample was re-heated to 900° F. (482° C.) in nitrogen and held for three hours. The atmosphere was then gradually changed to 1.1, 2.1, 4.2, and 8.4% oxygen in four stepwise increments. Each step was held for 30 minutes. The temperature was increased to 1000° F. (540° C.), the oxygen content was increased to 16.8%, and the material was held at 1000° F. (540° C.) for 6 hours. After cooling, ~0.28 wt % Ag was added via incipient wetness impregnation using an aqueous solution of silver nitrate. The Ag impregnated catalyst was dried at 250° F. (121° C.) for 4 hours. Subsequently, ~0.46 wt % Pt was added via incipient wetness impregnation using an aqueous solution of tetraamine platinum hydroxide. The resulting catalyst composition (Catalyst D) was dried at 250° F. (121° C.) for 5 hours, and lastly calcined in air at 610° F. (321° C.) for 1 hour.

Example 5—ZSM-5/Pt/Pr Catalyst Composition Synthesis (Catalyst E)

A sample of the zeolite support material synthesized in Example 4 in sodium form was calcined for 6 hours in nitrogen at 900° F. (482° C.). After cooling, the sample was re-heated to 900° F. (482° C.) in nitrogen and held for 3 hours. The atmosphere was then gradually changed to 1.1, 2.1, 4.2, and 8.4% oxygen in four stepwise increments. Each step was held for 30 minutes. The temperature was increased to 1000° F. (540° C.), the oxygen content was increased to 16.8%, and the material was held at 1000° F. (540° C.) for 6 hours. After cooling, ~0.36 wt % Pr was added via incipient wetness impregnation using an aqueous solution of praseodymium nitrate hexahydrate. The Pr impregnated catalyst was dried at 250° F. (121° C.) for 4 hours. Subsequently, ~0.53 wt % Pt was added via incipient wetness impregnation using an aqueous solution of tetraamine platinum hydroxide. The resulting catalyst composition (Catalyst E) was dried at 250° F. (121° C.) for overnight, and lastly calcined in air at 610° F. (321° C.) for 1 hour.

Example 6—ZSM-5/Pt Catalyst Composition Synthesis (Catalyst F)

A sample of the zeolite support material synthesized in Example 4 in sodium form was calcined for 6 hours in nitrogen at 900° F. (482° C.). After cooling, the sample was re-heated to 900° F. (482° C.) in nitrogen and held for 3 hours. The atmosphere was then gradually changed to 1.1, 2.1, 4.2, and 8.4% oxygen in four stepwise increments. Each step was held for 30 minutes. The temperature was increased to 1000° F. (540° C.), the oxygen content was increased to 16.8%, and the material was held at 1000° F. (540° C.) for 6 hours. After cooling, ~0.50 wt % Pt was added via incipient wetness impregnation using an aqueous solution of tetraamine platinum hydroxide. The resulting catalyst composition (Catalyst F) was dried at 250° F. (121° C.) overnights, and lastly calcined in air at 660° F. (321° C.) for 3 hours.

Example 7—Ag-MFI Catalyst Composition Synthesis (Catalyst G)

A synthesis mixture with ~22% solids was prepared from 9,400 g of deionized (DI) water, 535 g of 50% NaOH solution, 768 g of n-propyl amine 100% solution, 20 g of ZSM-5 seed crystals, 44 g of silver nitrate (99% solution), and 3,360 g of Sipernat™ 340 specialty silica were mixed in a 5-gal pail container and then charged into a 5-gal autoclave after mixing. The synthesis mixture had the following molar composition:

| | |
|---|---|
| $SiO_2/Al_2O_3$ | >800 |
| $H_2O/SiO_2$ | ~11 |
| $OH/SiO_2$ | ~0.17 |
| $Na/SiO_2$ | ~0.16 |
| n-PA/Si | ~0.25. |

The synthesis mixture was mixed and reacted at 230° F. (110° C.) at 250 rpm for 48 hours. The resulting reaction slurry was discharged and stored in a 5-gal pail container. The XRD pattern of the as-synthesized support material showed the typical pure phase of ZSM-5 topology. The SEM of the as-synthesized support material showed that the material was composed of a mixture of large crystals with size of ~1-2 micron. The resulting crystals had a $SiO_2/Al_2O_3$ molar ratio of ~1043, and a silver content of 0.95 wt %.

The synthesized support material was calcined for 6 hours in nitrogen at 900° F. (482° C.). After cooling, the sample was re-heated to 900° F. (482° C.) in nitrogen and held for three hours. The atmosphere was then gradually changed to 1.1, 2.1, 4.2, and 8.4% oxygen in four stepwise increments. Each step was held for 30 minutes. The temperature was increased to 1000° F. (540° C.), the oxygen content was increased to 16.8%, and the material was held at 1000° F. (540° C.) for 6 hours. After cooling, ~0.44 wt % Pt was added via incipient wetness impregnation using an aqueous solution of tetraamine platinum hydroxide. The resulting catalyst composition (Catalyst G) was dried at 250° F. (121° C.) overnight, calcined in air at 660° F. (349° C.) for 3 hours, and lastly calcined in air at 900° F. (482° C.) for 3 hours.

Example 8—Oxygen Rejuvenation of Catalyst A: Varying Temperature & Oxygen Concentration The initial performance of Catalyst A was tested in accordance with the following procedure. Catalyst A (0.5 g) was physically mixed with high-purity SiC (40-60 mesh) and loaded into a 9 mm ID, 13 mm OD, 22" (56 cm) long quartz reactor. The amount of SiC was adjusted so that the overall length of the catalyst bed was 6" (15 cm). The catalyst bed was held in place with quartz wool and the reactor void space was loaded with coarse SiC particles. The catalyst was dried for 2 hours under He (100 mL/min, 30 psig, 250° C.) then reduced for 4 hours under $H_2$ (200 mL/min, 60 psia (410 kPa), 500° C.).

A feed containing n-pentane, $H_2$, and balance He was introduced at the following conditions: 5.0 psia (34 kPa) $C_5H_{12}$, 2.5 psia (17 kPa) $H_2$, 3000 WHSV (g $C_5H_{12}$/g Pt $h^{-1}$), 60 psia total (410 kPa). The catalyst was de-edged at 550° C. for 8 hours and then tested at 575° C. for 15 hours to accumulate sufficient coke to deactivate the catalyst.

The same reactor as described above was then used to perform two series of in situ oxygen rejuvenation tests on the deactivated catalyst to study the effect of temperature and oxygen concentration during rejuvenation on catalyst performance. Each oxygen rejuvenation test was carried out by performing a number of rejuvenation cycles, with each rejuvenation cycle comprising 1) oxygen rejuvenation followed by 2) re-testing the performance of the rejuvenated catalyst using the n-pentane/$H_2$/He feed of the initial performance test at 575° C. for 15 hours.

During the performance test portion of each rejuvenation cycle, the normalized cyclopentadiene yield, determined on a carbon percentage basis, and the cyclic $C_5$ hydrocarbon selectivity, defined as the cyclic $C_5$ hydrocarbon yield on a carbon percentage basis divided by the sum of the $C_1$-$C_4$ hydrocarbon yield on a carbon percentage basis, were evaluated at t=12.3 hours.

Figure 1B:
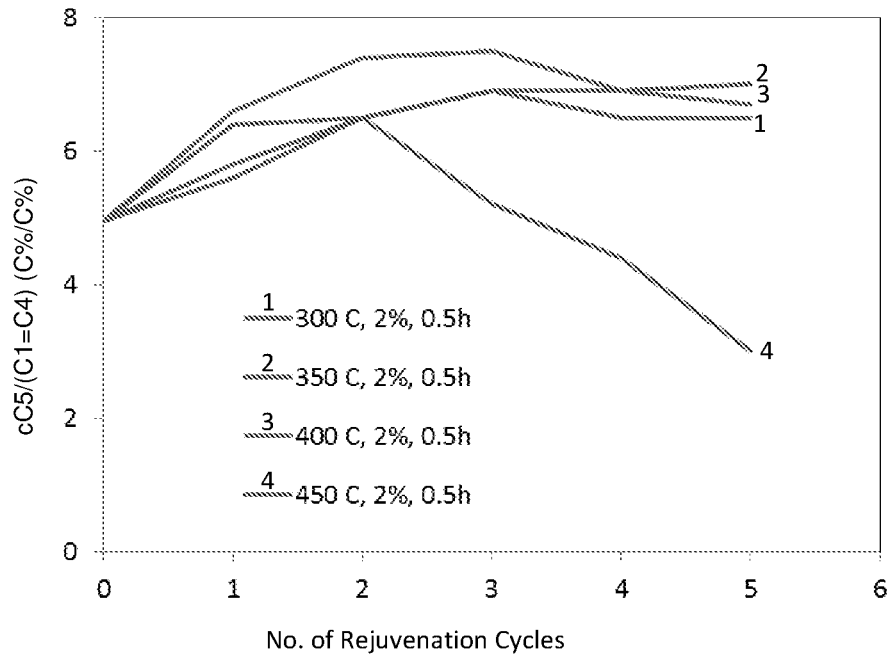
Figure 2A:
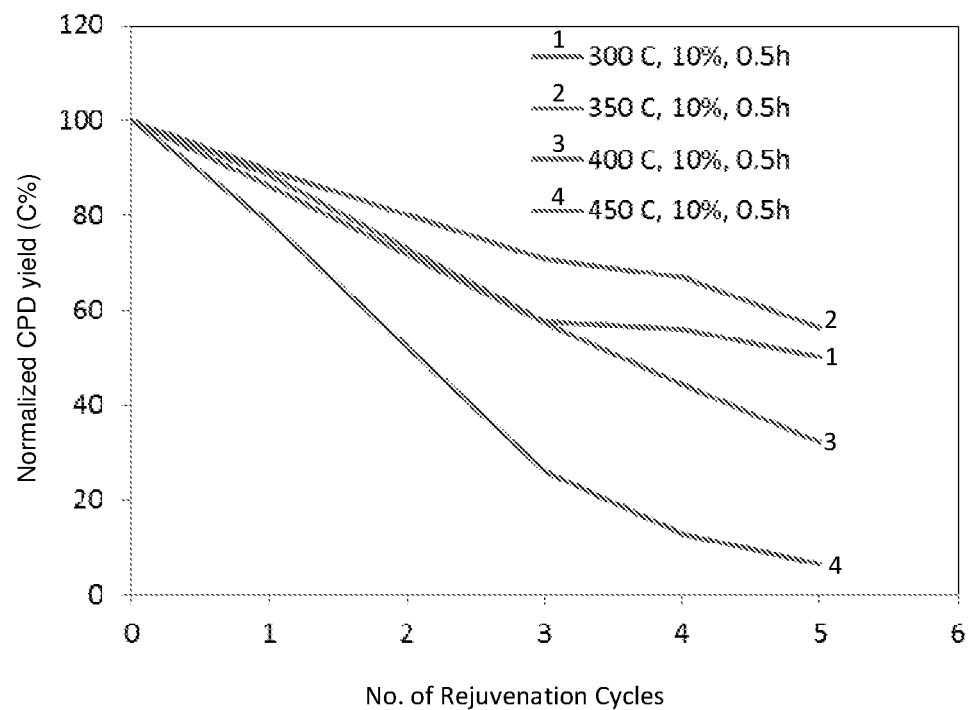
FIG. 2A and FIG. 2B show the normalized CPD yield and cyclic $C_5$ hydrocarbon selectivity against the number of rejuvenation cycles resulting from the performance evaluation conducted in Example 8 of catalyst rejuvenated using an oxygen-containing gaseous stream having an oxygen concentration of 10 vol % at a variety of temperatures.
Figure 2B:
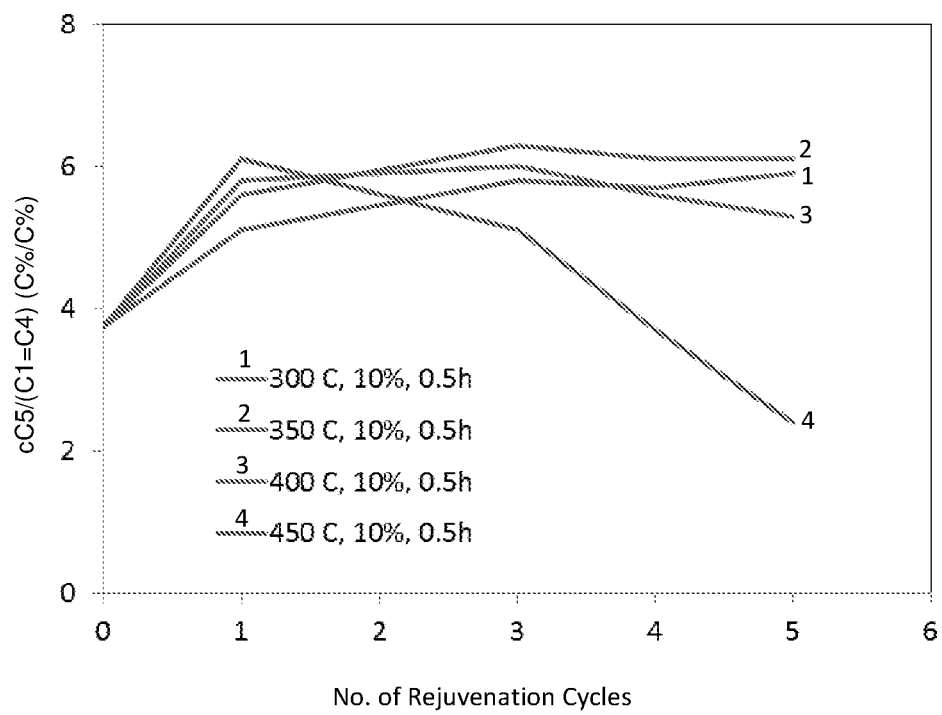

In the first series of oxygen rejuvenation tests, the catalyst was rejuvenated during each rejuvenation cycle by introducing an oxygen-containing gaseous stream (150 mL/min, 40 psia (276 kPa)) having an oxygen concentration of 2 vol % into the reactor bed for a duration of 0.5 hours at a temperature of 300° C., 350° C., 400° C., or 450° C. Performance results for the first series of tests plotted over five rejuvenation cycles are shown in FIG. 1A and FIG. 1B. In the second series of oxygen rejuvenation tests, the catalyst was rejuvenated during each rejuvenation cycle in the same manner as in the first series of tests, with the exception that the oxygen-containing gaseous stream had an increased oxygen concentration of 10 vol %. Performance results for the second series of tests plotted over five rejuvenation cycles are shown in FIG. 2A and FIG. 2B.

FIG. 1A, FIG. 1B, FIG. 2A, and FIG. 2B suggest that the preferred rejuvenation temperature of Catalyst A over the tested temperature span is in the range from 300–400° C., with 350° C. being especially preferred. Particularly, catalyst rejuvenated at a temperature in the range from 300–400° C. exhibited the least amount of cyclopentadiene yield loss as compared to catalyst rejuvenated at a higher temperature of 450° C., and also displayed maintained or even improved selectivity with each rejuvenation cycle. FIG. 1A, FIG. 1B, FIG. 2A, and FIG. 2B further suggest that varying the oxygen concentration in the oxygen-containing gaseous stream from 2 vol % to 10 vol % had little effect on the performance of Catalyst A.

Example 9—Oxygen Rejuvenation of Catalyst E: Varying Temperature

The initial performance of Catalyst E was tested in accordance with the following procedure. Catalyst E (0.2-0.8 g) was physically mixed with high-purity SiC (40-60 mesh) and loaded into a 9 mm ID, 13 mm OD, 22" (56 cm) long quartz reactor. The amount of SiC was adjusted so that the overall length of the catalyst bed was 6" (15 cm). The catalyst bed was held in place with quartz wool and the reactor void space was loaded with coarse SiC particles. The catalyst was dried for 2 hours under He (75 mL/min, 60 psia (410 kPa), 250° C.) then reduced for 4 hours under $H_2$ (150 mL/min, 60 psia (410 kPa), 500° C.).

A feed containing n-pentane, $H_2$, and balance He was introduced at the following conditions: 5.0 psia (34 kPa) $C_5H_{12}$, 2.5 psia (17 kPa) $H_2$, 3000 WHSV (g $C_5H_{12}$/g Pt $h^{-1}$), 60 psia total (410 kPa). The catalyst was de-edged at 550° C. for 8 hours and then tested at 575° C. for 15 hours to accumulate sufficient coke to deactivate the catalyst.

The same reactor as described above was used to perform a series of in situ oxygen rejuvenation tests on the deactivated catalyst to study the effect of temperature during rejuvenation on catalyst performance. The oxygen rejuvenation tests were carried out by performing a number of rejuvenation cycles, with each rejuvenation cycle comprising 1) oxygen rejuvenation followed by 2) re-testing the performance of the rejuvenated catalyst using the n-pentane/$H_2$/He feed of the initial performance test at 575° C. for 15 hours. In between the oxygen rejuvenation and performance test portion of each rejuvenation cycle, the catalyst bed was purged with He, ramped to 500° C. and held at 500° C. in $H_2$ for 1 hour.

During the performance test portion of each rejuvenation cycle, the normalized cyclopentadiene yield, determined on a carbon percentage basis, and the cyclic $C_5$ hydrocarbon selectivity, defined as the cyclic $C_5$ hydrocarbon yield on a carbon percentage basis divided by the sum of the $C_1$-$C_4$ hydrocarbon yield on a carbon percentage basis, were evaluated at t=12.3 hours.

The catalyst was rejuvenated during each rejuvenation cycle by introducing an oxygen-containing gaseous stream (150 mL/min, 40 psia (276 kPa)) having an oxygen concentration of 2 vol % into the reactor bed for a duration of 0.5 hours at a temperature of 300° C., 350° C., 400° C., 450° C., or 550° C. Performance results for the rejuvenation tests plotted over three rejuvenation cycles are shown in FIG. 3A and FIG. 3B.

Figure 3A:
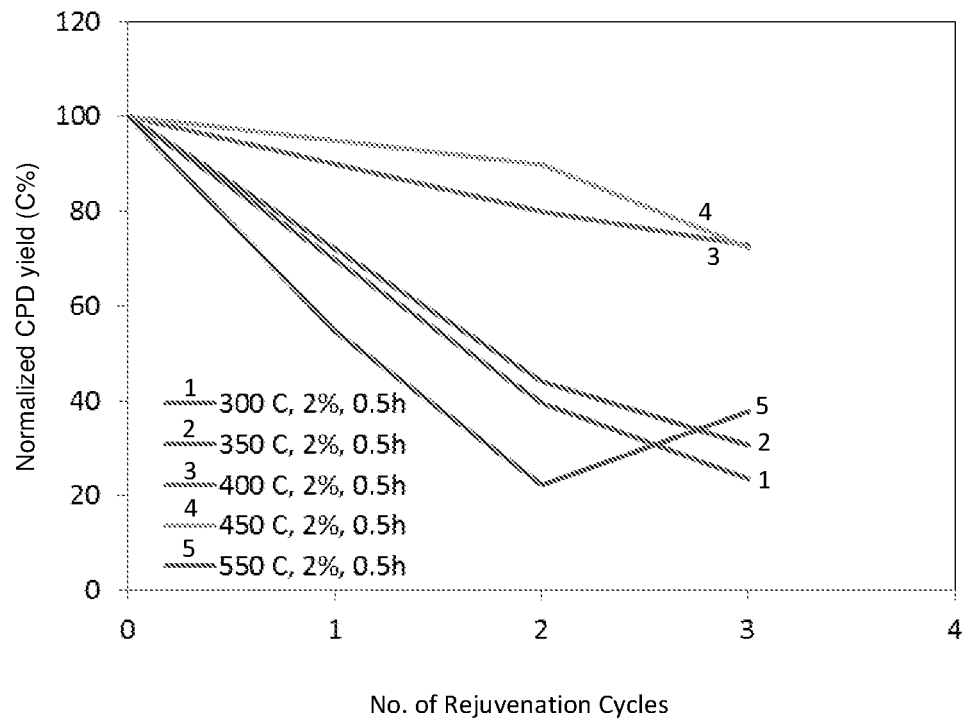
FIG. 3A and FIG. 3B show the normalized CPD yield and cyclic $C_5$ hydrocarbon selectivity against the number of rejuvenation cycles resulting from the performance evaluation conducted in Example 9 of catalyst rejuvenated using an oxygen-containing gaseous stream at a variety of temperatures.
Figure 3B:
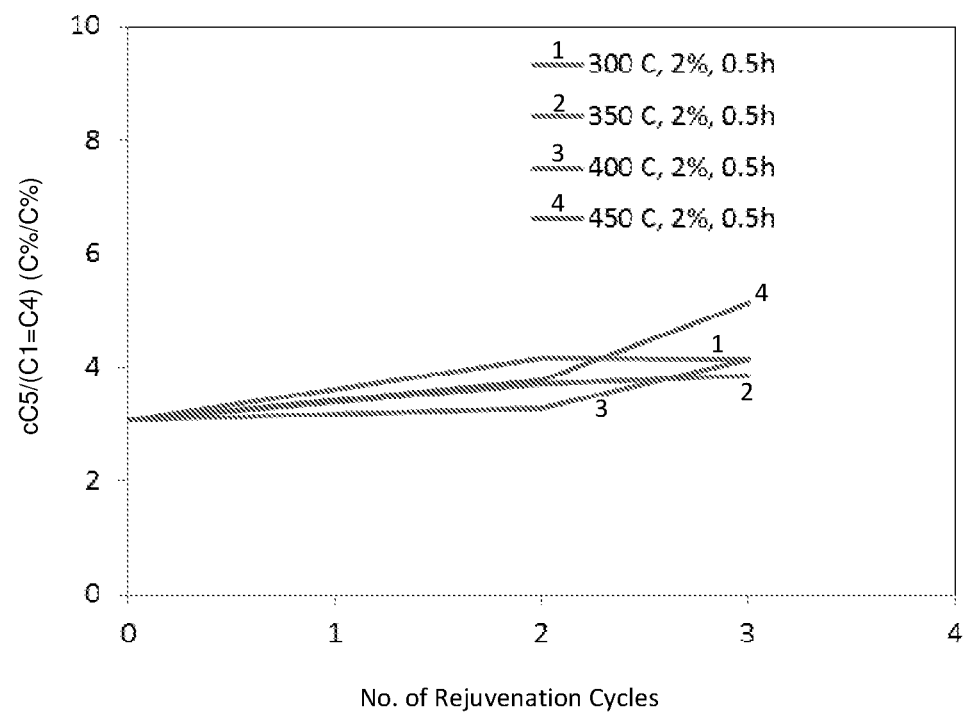

FIG. 3A and FIG. 3B suggest that the preferred rejuvenation temperature of Catalyst E over the tested temperature span is in the range from 400° C.-450° C. Particularly, catalyst rejuvenated at 400° C.-450° C. exhibited the least amount of cyclopentadiene yield loss as compared to catalyst rejuvenated at lower or higher temperatures. As also seen from FIG. 3A and FIG. 3B, the selectivity performance of Catalyst E remained relatively constant over a rejuvenation temperature range of 300° C.-450° C.

Example 10—Oxygen Rejuvenation of Catalyst F: Varying Temperature

The initial performance of Catalyst F was tested in accordance with the following procedure. Catalyst F (0.2-

0.8 g) was physically mixed with high-purity SiC (50-60 mesh) and loaded into a 9 mm ID, 13 mm OD, 22" (56 cm) long quartz reactor. The amount of SiC was adjusted so that the overall length of the catalyst bed was 6" (15 cm). The catalyst bed was held in place with quartz wool and the reactor void space was loaded with coarse SiC particles. The catalyst was dried for 2 hours under He (75 mL/min, 60 psia (410 kPa), 250° C.) then reduced for 4 hours under $H_2$ (150 mL/min, 60 psia (410 kPa), 500° C.).

A feed containing n-pentane, $H_2$, and balance He was introduced at the following conditions: 5.0 psia (34 kPa) $C_5H_{12}$, 2.5 psia (17 kPa) $H_2$, 3000 WHSV (g $C_5H_{12}$/g Pt $h^{-1}$), 60 psia total (410 kPa). The catalyst was de-edged at 550° C. for 8 hours and then tested at 575° C. for 15 hours to accumulate sufficient coke to deactivate the catalyst.

The same reactor as described above was then used to perform a series of in situ oxygen rejuvenation tests on the deactivated catalyst to study the effect of temperature during rejuvenation on catalyst performance. The oxygen rejuvenation tests were carried out by performing a number of rejuvenation cycles, with each rejuvenation cycle comprising 1) oxygen rejuvenation followed by 2) re-testing the performance of the rejuvenated catalyst using the n-pentane/$H_2$/He feed of the initial performance test at 575° C. for 15 hours. During the performance test portion of each rejuvenation cycle, the normalized cyclopentadiene yield, determined on a carbon percentage basis, and the cyclic $C_5$ hydrocarbon selectivity, defined as the cyclic $C_5$ hydrocarbon yield on a carbon percentage basis divided by the sum of the $C_1$-$C_4$ hydrocarbon yield on a carbon percentage basis, were evaluated at t=12.3 hours.

The catalyst was rejuvenated during each rejuvenation cycle by introducing an oxygen-containing gaseous stream (150 mL/min, 40 psia (276 kPa)) having an oxygen concentration of 2 vol % into the reactor bed for a duration of 0.5 hours at a temperature of 300° C., 350° C., 400° C., or 450° C. Performance results for the rejuvenation tests plotted over six rejuvenation cycles are shown in FIG. 4A and FIG. 4B.

Figure 4A:
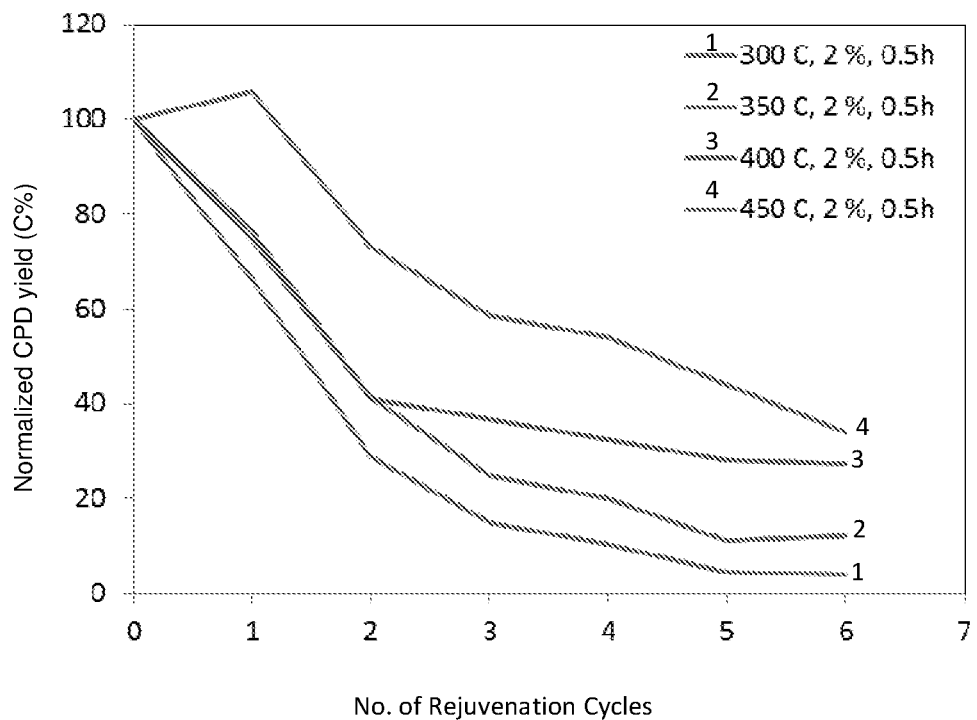
FIG. 4A and FIG. 4B show the normalized CPD yield and cyclic $C_5$ hydrocarbon selectivity against the number of rejuvenation cycles resulting from the performance evaluation conducted in Example 10 of catalyst rejuvenated using an oxygen-containing gaseous stream at a variety of temperatures.
Figure 4B:
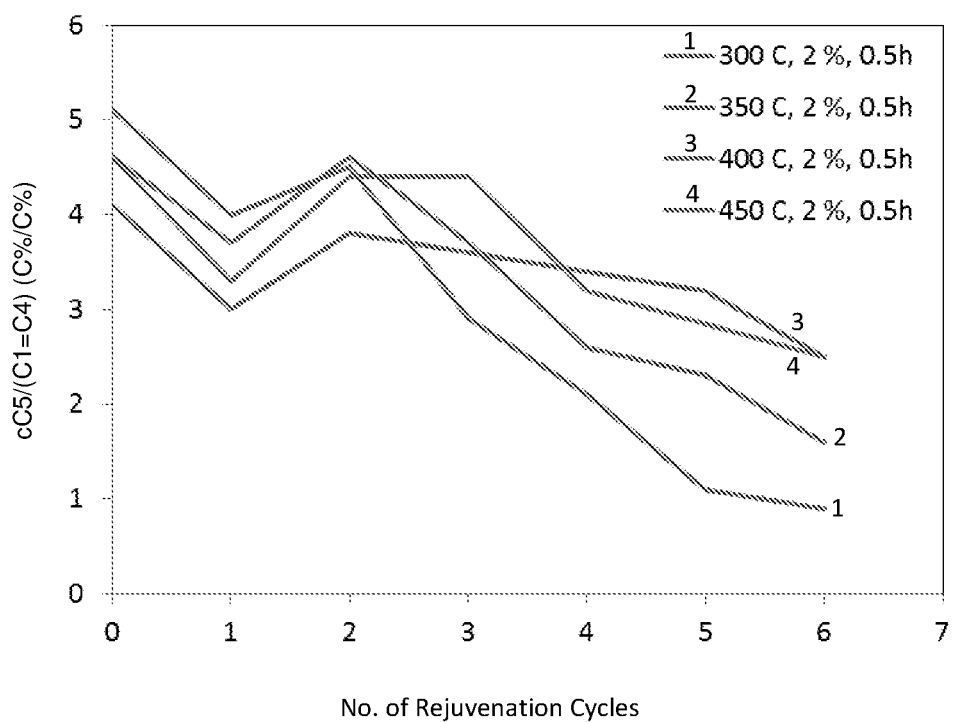

FIG. 4A and FIG. 4B suggest that the performance of Catalyst F was robust over the tested temperature span, with moderate yield improvement observed with increasing temperature over the tested range of 300° C.-450° C. and comparable selectivity performance observed over the tested range of 300° C.-450° C.

Example 11—Oxygen Rejuvenation of Catalyst G: Varying Temperature

The initial performance of Catalyst G was tested in accordance with the following procedure. Catalyst G (0.2-0.8 g) was physically mixed with high-purity SiC (50-60 mesh) and loaded into a 9 mm ID, 13 mm OD, 22" (56 cm) long quartz reactor. The amount of SiC was adjusted so that the overall length of the catalyst bed was 6" (15 cm). The catalyst bed was held in place with quartz wool and the reactor void space was loaded with coarse SiC particles. The catalyst was dried for 2 hours under He (75 mL/min, 60 psia (410 kPa), 250° C.) then reduced for 4 hours under $H_2$ (150 mL/min, 60 psia (410 kPa), 500° C.).

A feed containing n-pentane, $H_2$, and balance He was introduced at the following conditions: 5.0 psia (34 kPa) $C_5H_{12}$, 2.5 psia (17 kPa) $H_2$, 3000 WHSV (g $C_5H_{12}$/g Pt $h^{-1}$), 60 psia total (410 kPa). The catalyst was de-edged at 550° C. for 8 hours and then tested at 575° C. for 15 hours to accumulate sufficient coke to deactivate the catalyst.

The same reactor as described above was then used to perform a series of in situ oxygen rejuvenation tests on the deactivated catalyst to study the effect of temperature during rejuvenation on catalyst performance. The oxygen rejuvenation tests were carried out by performing a number of rejuvenation cycles, with each rejuvenation cycle comprising 1) oxygen rejuvenation followed by 2) re-testing the performance of the rejuvenated catalyst using the n-pentane/$H_2$/He feed of the initial performance test at 575° C. for 15 hours. During the performance test portion of each rejuvenation cycle, the normalized cyclopentadiene yield, determined on a carbon percentage basis, and the cyclic $C_5$ hydrocarbon selectivity, defined as the cyclic $C_5$ hydrocarbon yield on a carbon percentage basis divided by the sum of the $C_1$-$C_4$ hydrocarbon yield on a carbon percentage basis, were evaluated at t=12.3 hours.

The catalyst was rejuvenated during each rejuvenation cycle by introducing an oxygen-containing gaseous stream (150 mL/min, 40 psia (276 kPa)) having an oxygen concentration of 2 vol % into the reactor bed for a duration of 0.5 hours at a temperature of 300° C., 350° C., 400° C., or 450° C. Performance results for the rejuvenation tests plotted over six rejuvenation cycles are shown in FIG. 5A and FIG. 5B.

Figure 5A:
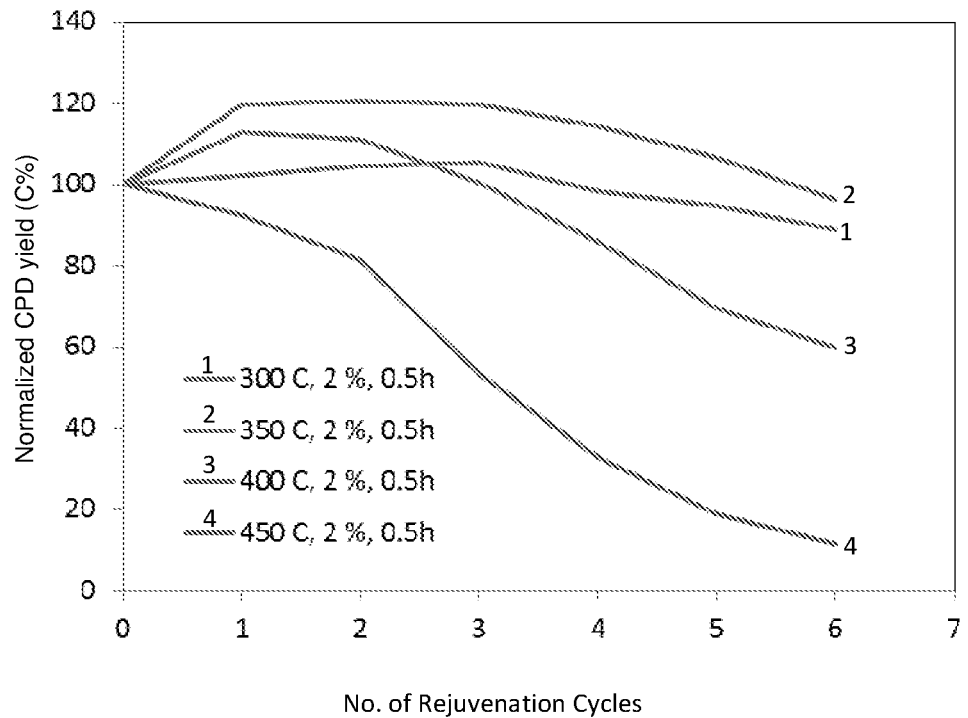
FIG. 5A and FIG. 5B show the normalized CPD yield and cyclic $C_5$ hydrocarbon selectivity against the number of rejuvenation cycles resulting from the performance evaluation conducted in Example 11 of catalyst rejuvenated using an oxygen-containing gaseous stream at a variety of temperatures.
Figure 5B:
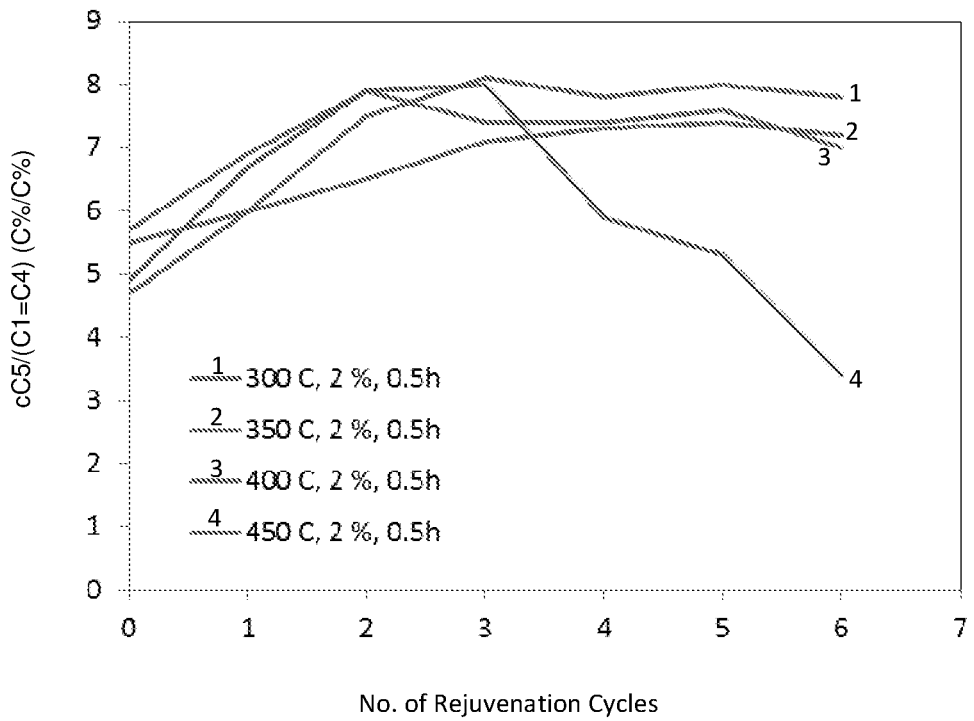

FIG. 5A and FIG. 5B suggest that the preferred rejuvenation temperature of Catalyst G ranges from 300° C.-350° C. Particularly, catalyst rejuvenated at 300-350° C. exhibited the least amount of cyclopentadiene yield loss over successive rejuvenation cycles as compared to catalyst rejuvenated at higher temperatures. As also seen from FIG. 5A and FIG. 5B, the selectivity performance of Catalyst G remained relatively constant over the tested rejuvenation temperature range of 300° C.-450° C.

Example 12—Oxygen Rejuvenation of Catalyst B: Varying Temperature & Time Duration The initial performance of Catalyst B was tested in accordance with the following procedure. The catalyst (0.5 g) was physically mixed with high-purity SiC (40-60 mesh) and loaded into a 9 mm ID, 13 mm OD, 22" (56 cm) long quartz reactor. The amount of SiC was adjusted so that the overall length of the catalyst bed was 6" (15 cm). The catalyst bed was held in place with quartz wool and the reactor void space was loaded with coarse SiC particles. The catalyst was dried for 2 hours under He (100 mL/min, 30 psig, 250° C.) then reduced for 4 hours under $H_2$ (200 mL/min, 60 psia (410 kPa), 500° C.).

The catalyst was tested for initial performance with a feed containing n-pentane, $H_2$, and balance He at the following conditions: 5.0 psia (34 kPa) $C_5H_{12}$, 2.5 psia (17 kPa) $H_2$, 3000 WHSV (g $C_5H_{12}$/g Pt $h^{-1}$), 60 psia total (410 kPa). The catalyst was de-edged at 550° C. for 8 hours and then tested at 575° C. for 15 hours to accumulate sufficient coke to deactivate the catalyst.

The same reactor as described above was used to perform two series of in situ oxygen rejuvenation tests on the deactivated catalyst to study the effect of temperature and time duration during rejuvenation on catalyst performance Each oxygen rejuvenation test was carried out by performing a number of rejuvenation cycles, with each rejuvenation cycle comprising 1) oxygen rejuvenation followed by 2) re-testing the performance of the rejuvenated catalyst using the n-pentane/$H_2$/He feed of the initial performance test at 575° C. for 15 hours. During the performance test portion of each rejuvenation cycle, the normalized cyclopentadiene yield, determined on a carbon percentage basis, and the cyclic $C_5$ hydrocarbon selectivity, defined as the cyclic $C_5$ hydrocarbon yield on a carbon percentage basis divided by the sum of the $C_1$-$C_4$ hydrocarbon yield on a carbon percentage basis, were evaluated at t=12.3 hours.

Figure 6A:
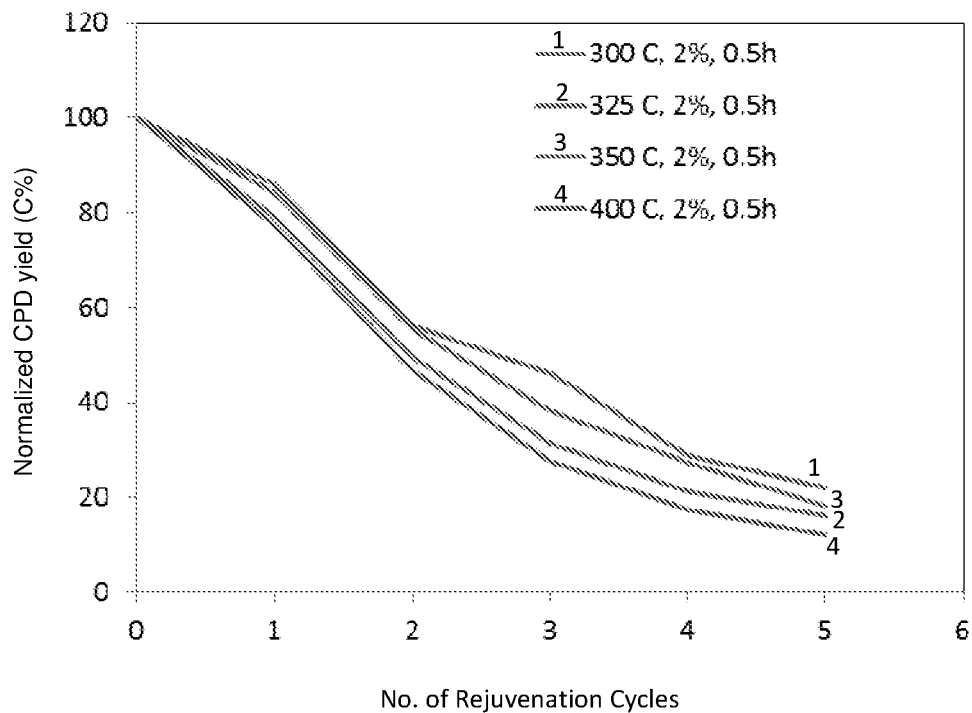
FIG. 6A and FIG. 6B show the normalized CPD yield and cyclic $C_5$ hydrocarbon selectivity against the number of rejuvenation cycles resulting from the performance evaluation conducted in Example 12 of catalyst rejuvenated using an oxygen-containing gaseous stream at a variety of temperatures for a time period of 0.5 hours per rejuvenation cycle.
Figure 6B:
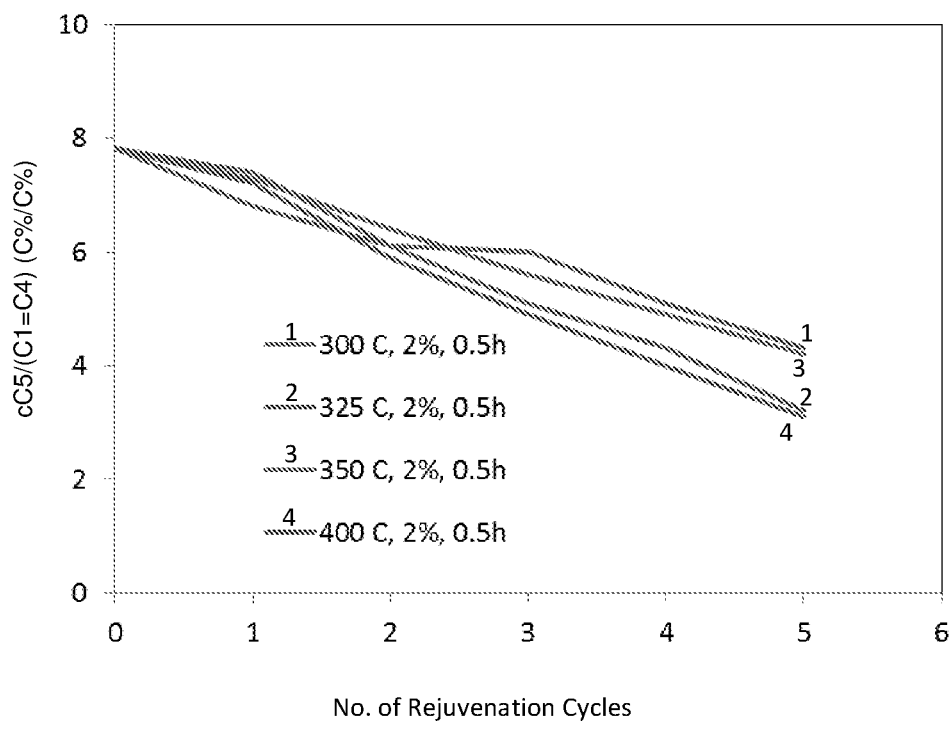
Figure 7A:
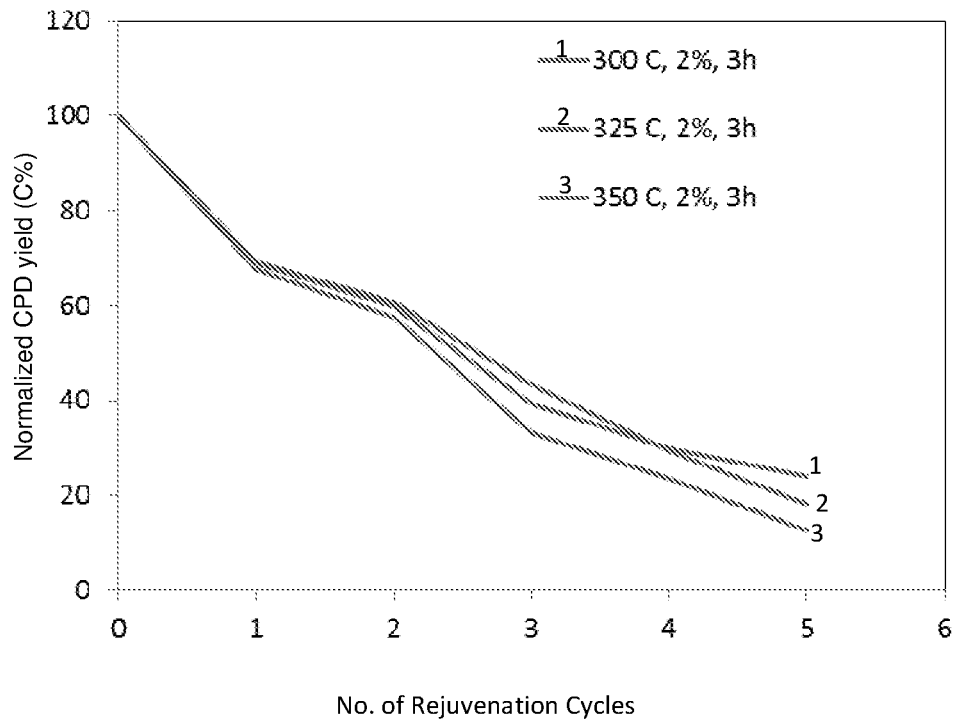
FIG. 7A and FIG. 7B show the normalized CPD yield and cyclic $C_5$ hydrocarbon selectivity against the number of rejuvenation cycles resulting from the performance evaluation conducted in Example 12 of catalyst rejuvenated using an oxygen-containing gaseous stream at a variety of temperatures for a time period of 3 hours per rejuvenation cycle.
Figure 7B:
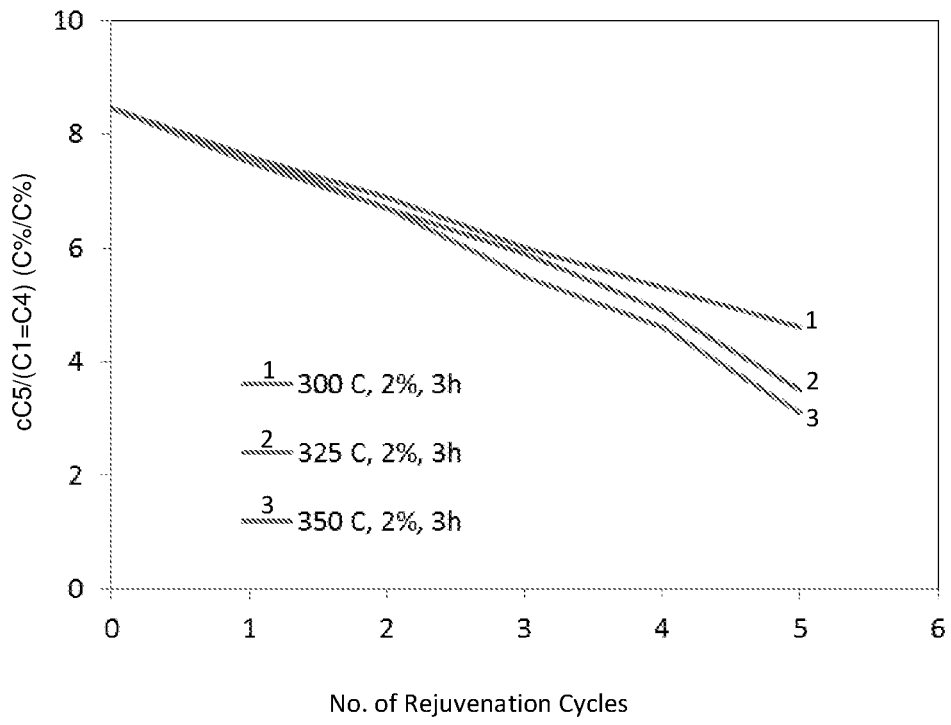

In the first series of oxygen rejuvenation tests, the catalyst was rejuvenated during each rejuvenation cycle by introducing an oxygen-containing gaseous stream (150 mL/min, 40 psia (276 kPa)) having an oxygen concentration of 2 vol % into the reactor bed for a duration of 0.5 hours at a temperature of 300° C., 325° C., 350° C., or 400° C. Performance results for the first series of tests plotted over five rejuvenation cycles are shown in FIG. 6A and FIG. 6B. In the second series of oxygen rejuvenation tests, the catalyst was rejuvenated during each rejuvenation cycle in the same manner as in the first series of tests, with the exception that time duration of the rejuvenation was increased to 3 hours. Performance results for the second series of tests plotted over five rejuvenation cycles are shown in FIG. 7A and FIG. 7B.

FIG. 6A, FIG. 6B, FIG. 7A, and FIG. 7B suggest that the rejuvenation temperature had little effect on the performance of Catalyst B over the tested rejuvenation temperature range of 300° C.-400° C. Particularly, catalyst rejuvenated across the entire range from 300° C.-400° C. exhibited comparable cyclopentadiene yield and selectivity losses with each rejuvenation cycle. FIG. 6A, FIG. 6B, FIG. 7A, and FIG. 7B further suggest that varying the time duration of each rejuvenation cycle from 0.5 hours to 3 hours also had little effect on the performance of Catalyst B.

Example 13—Carbon Dioxide Rejuvenation of Catalyst C

The initial performance of Catalyst C was tested in accordance with the following procedure. Catalyst C (0.5 g) was physically mixed with high-purity SiC (40-60 mesh) and loaded into a ⅜" (0.95 cm) outer diameter and an 18" (46 cm) length stainless steel reactor. The amount of SiC was adjusted so that the overall length of the catalyst bed was 6" (15 cm). The catalyst bed was held in place with quartz wool and the reactor void space was loaded with coarse SiC particles. The catalyst was dried for 2 hours under He (100 mL/min, 60 psia (410 kPa), 250° C.) then reduced for 4 hours under $H_2$ (200 mL/min, 60 psia (410 kPa), 500° C.).

A feed containing 1-pentene, $H_2$, and balance He was introduced at the following conditions: 7.0 psia (48 kPa) $C_5H_{10}$, 14 psia (97 kPa) $H_2$, 30 WHSV (g $C_5H_{10}$/g Pt $h^{-1}$), 60 psia total (410 kPa). The catalyst was held on-oil at 575° C. for 30 hours to accumulate sufficient coke to deactivate the catalyst.

Post-reaction, the deactivated catalyst material was rejuvenated in situ via carbon dioxide coke removal in accordance with the reverse Boudouard reaction, as shown below:

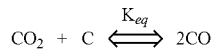

$$CO_2 + C \underset{}{\overset{K_{eq}}{\rightleftharpoons}} 2CO$$

First, the catalyst was dried with flowing nitrogen (800 ml/min, 40 psia) at 250° C. for 2 hours time-on-steam (TOS). At 2 hours TOS, the catalyst was subjected to a carbon dioxide treatment by flowing 100 vol % $CO_2$ (500 ml/min) over the catalyst from 2 hours TOS until 6 hours TOS. During the carbon dioxide treatment, the temperature was ramped to 600° C. from 2 hours TOS to 4 hours TOS and held at 600° C. from 4 hours TOS to 6 hours TOS. The $CO_2$ stream was discontinued at 6 hours TOS.

Figure 8:
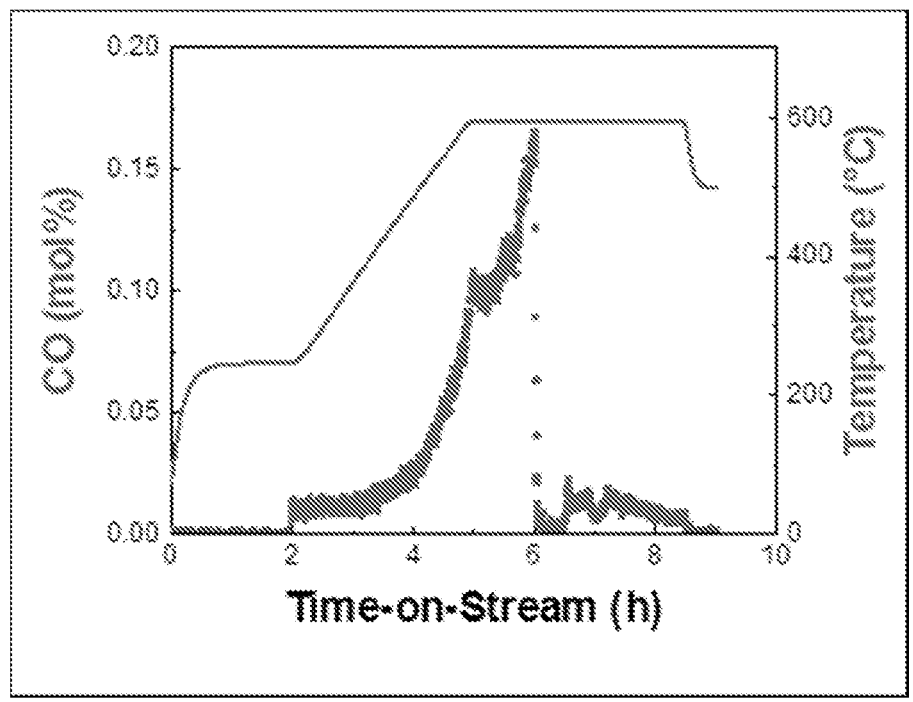
FIG. 8 shows the CO concentration and reactor temperature against time on stream (T.O.S.) resulting from the carbon dioxide rejuvenation conducted in Example 13.

FIG. 8 depicts the CO concentration and temperature in the reactor as a function of. TOS. FIG. 8 shows that the CO concentration increased from 2 hours TOS to 6 hours TOS, during the period of $CO_2$ flow, and sharply decreased at 6 hours TOS when $CO_2$ flow was discontinued. These results indicate that the carbon dioxide treatment was effective in removing coke from the catalyst over the tested temperature range.

Example 14—Oxygen Rejuvenation & Subsequent Hydrogen Treatment of Catalyst D: Varying Temperature The initial performance of Catalyst D was tested in accordance with the following procedure. Catalyst D (0.5 g) was physically mixed with high-purity SiC (40-60 mesh) and loaded into a 9 mm ID, 13 mm OD, 22" (56 cm) long quartz reactor. The amount of SiC was adjusted so that the overall length of the catalyst bed was 6" (15 cm). The catalyst bed was held in place with quartz wool and the reactor void space was loaded with coarse SiC particles. The catalyst was dried for 2 hours under He (75 mL/min, 60 psia (410 kPa), 250° C.) then reduced for 4 hours under $H_2$ (150 mL/min, 60 psia (410 kPa), 500° C.).

A feed containing n-pentane, $H_2$, and balance He was introduced at the following conditions: 5.0 psia (34 kPa) $C_5H_{12}$, 2.5 psia (17 kPa) $H_2$, 3000 WHSV (g $C_5H_{12}$/g Pt $h^{-1}$), 60 psia total (410 kPa). The catalyst was tested at 600° C. for 20 hours to accumulate sufficient coke to deactivate the catalyst.

The same reactor as described above was used to perform a series of in situ oxygen rejuvenation tests on the deactivated catalyst to study the effect of oxygen rejuvenation temperature and a subsequent hydrogen treatment step on catalyst performance Each oxygen rejuvenation test was carried out by performing a number of rejuvenation cycles, with each rejuvenation cycle comprising 1) oxygen rejuvenation followed by 2) hydrogen treatment followed by 3) re-testing the performance of the rejuvenated catalyst using the n-pentane/$H_2$/He feed of the initial performance test at 575° C. for 15 hours. In between the oxygen rejuvenation and hydrogen treatment portion of each rejuvenation cycle, the catalyst bed was purged with He.

During the performance test portion of each rejuvenation cycle, the normalized cyclopentadiene yield, determined on a carbon percentage basis, and the cyclic $C_5$ hydrocarbon selectivity, defined as the cyclic $C_5$ hydrocarbon yield on a carbon percentage basis divided by the sum of the $C_1$-$C_4$ hydrocarbon yield on a carbon percentage basis, were evaluated at t=12.3 hours.

Oxygen rejuvenation was carried out during each rejuvenation cycle by introducing an oxygen-containing gaseous stream (150 ml/min, 40 psia (276 kPa)) having an oxygen concentration of 2 vol % into the reactor bed for a duration of 4 hours at a temperature of 400° C., 450° C., or 500° C. Hydrogen treatment was carried out during each rejuvenation cycle by ramping the temperature to 600° C. and holding the temperature at 600° C. in the presence of $H_2$ for 4 hours. Performance results for the first series of tests plotted over two rejuvenation cycles are shown in FIG. 9A and FIG. 9B.

Figure 9A:
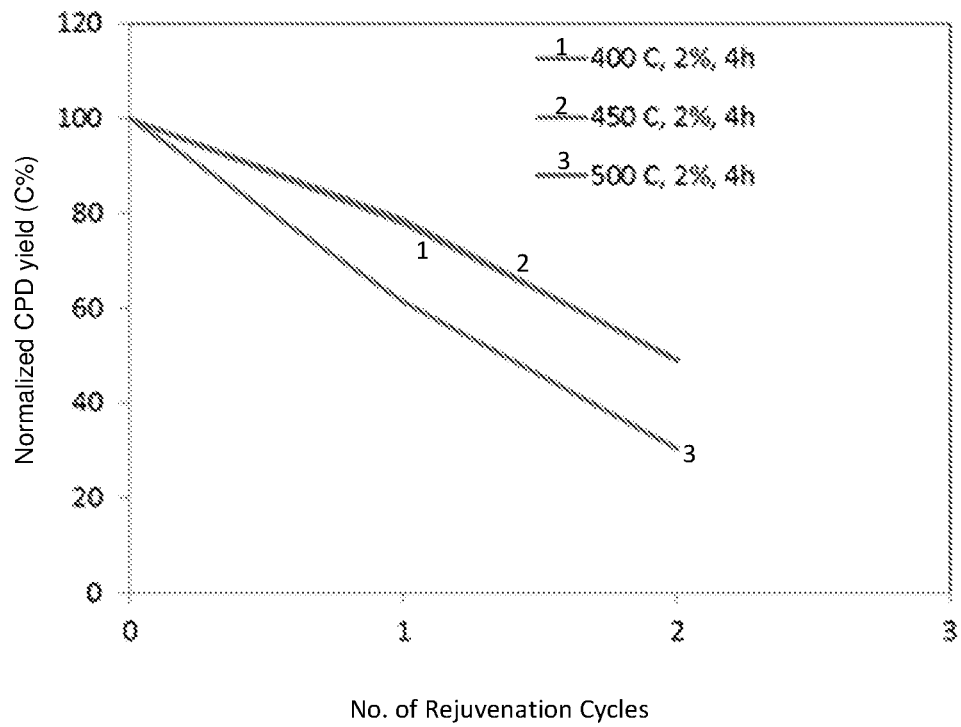
FIG. 9A and FIG. 9B show the normalized CPD yield and cyclic $C_5$ hydrocarbon selectivity against the number of rejuvenation cycles resulting from the performance evaluation conducted in Example 14 of catalyst subjected to a hydrogen treatment subsequent to oxygen rejuvenation in each rejuvenation cycle.
Figure 9B:
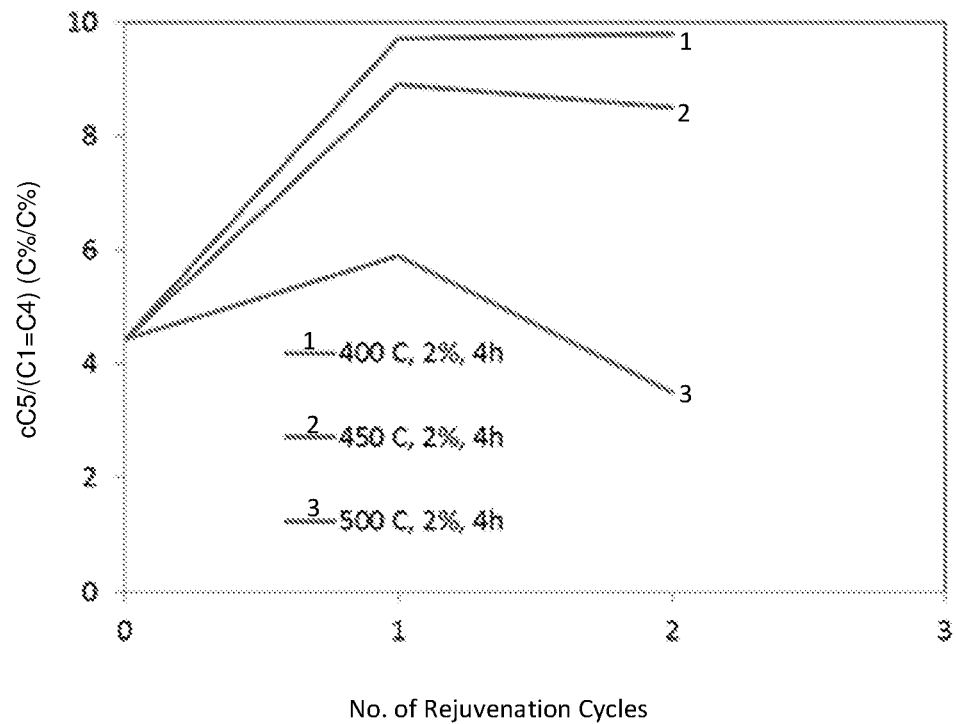

FIG. 9A and FIG. 9B suggest that the preferred oxygen rejuvenation temperature of Catalyst D when subjected to a subsequent hydrogen treatment step over the tested temperature span was in the range from 400° C.-450° C. Particularly, catalyst rejuvenated at 400° C.-450° C. exhibited the least amount of cyclopentadiene yield loss as compared to catalyst rejuvenated at higher temperature. As also seen from FIG. 9A and FIG. 9B, the selectivity performance of Catalyst D increased at a rejuvenation temperature range of 400° C.-450° C.

Example 15—Oxygen Rejuvenation & Prior Hydrogen Treatment of Catalyst A

The initial performance of Catalyst A was tested in accordance with the following procedure. The catalyst (0.25 g) was physically mixed with high-purity SiC (40-60 mesh) and loaded into a 14 mm ID, 19 mm OD, 28.5" (72 cm) long quartz reactor. The amount of SiC was adjusted so that the overall length of the catalyst bed was 6" (15 cm). The catalyst bed was held in place with quartz wool and the reactor void space was loaded with coarse SiC particles. Four such reactors produced and connected in series such that the gaseous feed flowed through reactor 1, 2, 3, and then 4. The catalyst was dried for 1 hour under He (1000 mL/min, 5 psig, 250° C.) then reduced for 4 hours under $H_2$ (1000 mL/min, 20 psia (137 kPa), 500° C.).

The catalyst was tested for initial performance with a feed containing n-pentane, $H_2$, and balance He at the following outlet conditions: 3.5 psia (24 kPa) $C_5H_{12}$, 3.5 psia (24 kPa) $H_2$, 10 WHSV (g $C_5H_{12}$/g Pt $h^{-1}$), 20 psia total (137 kPa). The catalyst was tested at 550° C. for 50 hours to accumulate sufficient coke to deactivate the catalyst.

Post-reaction, a hydrogen treatment was performed by flowing $H_2$ (60 psia (410 kPa), 500 sccm) over the catalyst for 0.5 hours at 550° C. The reactor system was purged with $N_2$ (1000 sccm) for 1 hour and temperature reduced to 350° C. Oxygen rejuvenation was then carried out by introducing an oxygen-containing gaseous stream (48 sccm air, 952 sccm $N_2$) having an oxygen concentration of 1 vol % into the reactor bed for a duration of 2 hours. The system was purged again, then brought back on-oil at 550° C. to re-test the catalyst performance.

Figure 10:
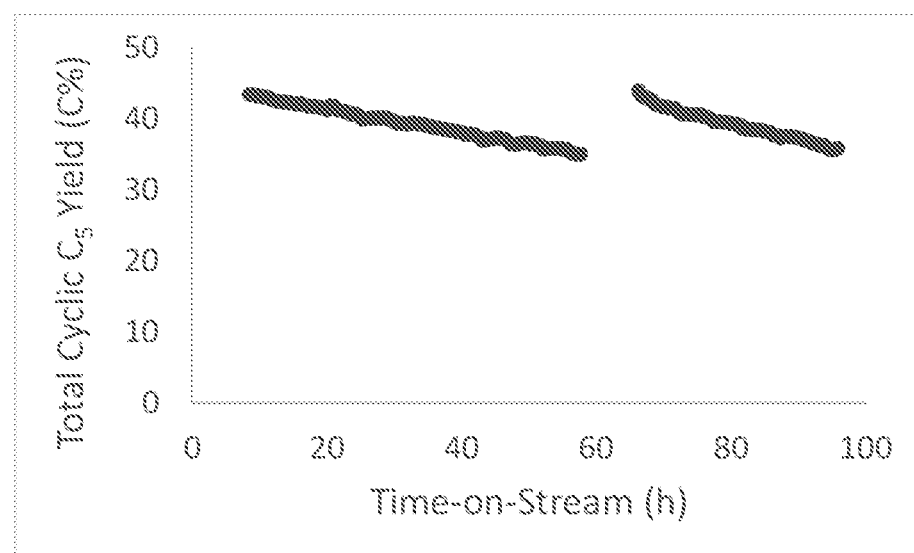
FIG. 10 shows the normalized CPD yield against TOS from the initial and post-rejuvenation performance evaluations conducted in Example 15 of catalyst subjected to a hydrogen treatment prior to oxygen rejuvenation.

FIG. 10 shows the normalized total cyclic $C_5$ yield after reactor 4, determined on a carbon percentage basis, as a function of TOS during the initial 50 hour performance test and during the performance test after the hydrogen treatment and oxygen rejuvenation. FIG. 10 demonstrates that the cyclization activity of the catalyst was fully recovered after hydrogen treatment and oxygen rejuvenation.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. For example, the compositions described herein may be free of any component, or composition not expressly recited or disclosed herein. Any method may lack any step not recited or disclosed herein. Likewise, the term "comprising" is considered synonymous with the term "including." And whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

The invention claimed is:

1. A process for rejuvenating a deactivated catalyst comprising at least one Group 10 metal and a microporous crystalline metallosilicate, the process comprising the steps of:
    (a) contacting the catalyst with an oxygen-containing gaseous stream under conditions comprising a temperature ranging from about 250° C. to about 375° C. and a pressure of up to about 100 bar; and
    (b) optionally, reducing the catalyst to obtain a rejuvenated catalyst.

2. The process claim 1, wherein the at least one Group 10 metal comprises platinum.

3. The process of any claim 1, wherein the catalyst further comprises one or more additional metals selected from the group consisting of Group 1 metals, Group 2 metals, Group 8 metals, Group 9 metals, Group 11 metals, and mixtures or combinations thereof.

4. The process of claim 3, wherein the one or more additional metals is selected from the group consisting of sodium, copper, silver, and mixtures or combinations thereof.

5. The process of claim 4, wherein the contacting temperature of step (a) ranges from about 300° C. to about 350° C.

6. The process of claim 1, wherein the microporous crystalline metallosilicate is an aluminosilicate selected from the group consisting of ZSM-5, ZSM-11, ZSM-22, ZSM-23, ZSM-35, ZSM-48, ZSM-50, ZSM-57, ZSM-58, a MCM-22 family material, and mixtures or combinations of two or more thereof.

7. The process of claim 6, wherein the aluminosilicate is ZSM-5.

8. The process of claim 1, wherein the catalyst further comprises a binder comprising one or more of silica, titania, zirconia, metal silicates of Group 1 or Group 13 of the Periodic Table, carbides, nitrides, aluminum phosphate, aluminum molybdate, aluminate, surface passivated alumina, and mixtures thereof.

9. The process of claim 1, wherein step (b) comprises contacting the catalyst with a hydrogen-containing gaseous stream under conditions comprising a temperature ranging from about 200° C. to about 800° C. and a pressure of up to about 100 bar.

10. The process of claim 1, further comprising the additional step of: (c) contacting the catalyst with a hydrogen-containing gaseous stream prior to the contacting of step (a), wherein the catalyst is contacted with the hydrogen-containing gaseous stream under conditions comprising a temperature ranging from about 200° C. to about 800° C. and a pressure of up to about 100 bar.

11. The process of claim 1, wherein the oxygen-containing gaseous stream comprises a member selected from the group consisting of $O_2$, $O_3$, nitrogen oxides, $CO_2$, and mixtures or combinations thereof.

12. The process of claim 11, wherein the contacting of step (a) comprises:
    (i) contacting the catalyst with a first gaseous stream comprising $CO_2$; and
    (ii) subsequently contacting the catalyst with a second gaseous stream comprising a member selected from the group consisting of $O_2$, $O_3$, nitrogen oxides, and mixtures or combinations thereof.

13. The process of claim 1, wherein the oxygen-containing gaseous stream has an oxygen concentration ranging from about 0.1 volume percent to about 20 volume percent.

14. The process of claim 1, wherein the oxygen-containing gaseous stream is supplied to the contacting of step (a) at a WHSV ranging from about 1 to about 10,000.

15. The process of claim 1, further comprising the step of increasing the temperature during the contacting of step (a).

16. The process of claim 1, further comprising the step of increasing the oxygen partial pressure and/or oxygen concentration of the oxygen-containing gaseous stream during the contacting of step (a).

17. The process of claim 1, wherein the contacting of step (a) has a time duration of about 5 hours or less.

18. A process for rejuvenating a deactivated catalyst comprising at least one Group 10 metal, at least one rare earth metal, and a microporous crystalline metallosilicate, the process comprising the steps of:
(a) contacting the catalyst with an oxygen-containing gaseous stream under conditions comprising a temperature ranging from about 250° C. to about 500° C. and a pressure of up to about 100 bar; and
(b) optionally, reducing the catalyst to obtain a rejuvenated catalyst.

19. The process of claim 18, wherein the contacting of step (a) comprises:
(i) contacting the catalyst with a first gaseous stream comprising $CO_2$; and
(ii) subsequently contacting the catalyst with a second gaseous stream comprising a member selected from the group consisting of $O_2$, $O_3$, nitrogen oxides, and mixtures or combinations thereof.

20. The process of claim 18, further comprising the step of increasing the oxygen partial pressure and/or oxygen concentration of the oxygen-containing gaseous stream during the contacting of step (a).

21. A process for the chemical conversion of a hydrocarbon feedstock, the process comprising the steps of:
(I) contacting a hydrocarbon feedstock with a catalyst comprising at least one Group 10 metal and a microporous crystalline metallosilicate in a reaction zone to form a hydrocarbon reaction product;
(II) forming deactivated catalyst from the catalyst;
(III) rejuvenating the deactivated catalyst in accordance with the process of claim 1; and
(IV) optionally, periodically regenerating the deactivated catalyst.

22. The process of claim 21, further comprising the additional step of (V) purging any combustible gas, including hydrocarbon feedstock and hydrocarbon reaction product, from the deactivated and/or rejuvenated catalyst.

23. The process of claim 21, wherein the rejuvenation of step (III) is performed in the reaction zone.

24. The process of claim 21, wherein the rejuvenation of step (III) is performed in a separate rejuvenation zone apart from the reaction zone.

25. The process of claim 21, wherein the chemical conversion comprises one or more of the following:
i. the conversion of acyclic $C_5$ hydrocarbons to cyclic $C_5$ hydrocarbons;
ii. the conversion of acyclic $C_{6+}$ hydrocarbons to aromatic $C_{6+}$ hydrocarbons;
iii. the conversion of $C_2$-$C_5$ hydrocarbons to $C_{6+}$ aromatic; and/or
iv. the dehydrogenation of paraffins to olefins and/or dienes.

* * * * *